United States Patent [19]

Schubert et al.

[11] Patent Number: 4,775,664

[45] Date of Patent: Oct. 4, 1988

[54] SILANE DERIVATIVES, AGENTS CONTAINING THEM, AND THEIR USE AS PESTICIDES

[75] Inventors: Hans H. Schubert, Frankfurt am Main; Gerhard Salbeck, Hofheim am Taunus; Walter Lüders, Heusenstamm; Werner Knauf, Eppstein; Anna Waltersdorfer, Frankfurt am Main, all of Fed. Rep. of Germany

[73] Assignee: Hoechst Aktiengesellschaft, Frankfurt am Main, Fed. Rep. of Germany

[21] Appl. No.: 36,575

[22] Filed: Apr. 10, 1987

[30] Foreign Application Priority Data

May 31, 1986 [DE] Fed. Rep. of Germany ....... 3618354

[51] Int. Cl.$^4$ .................. A01N 55/00; C07F 7/08; C07F 7/10; C07F 9/58
[52] U.S. Cl. ..................... 514/63; 344/229; 346/14; 556/406; 556/445; 556/448; 556/465
[58] Field of Search .......... 546/14; 544/229; 514/63; 556/406, 445, 448, 465

[56] References Cited

U.S. PATENT DOCUMENTS

| | | | |
|---|---|---|---|
| 3,334,123 | 8/1967 | Culpepper | 556/448 |
| 3,362,933 | 1/1968 | Culpepper | 556/448 |
| 3,370,790 | 11/1978 | Clark | 260/448.2 B |
| 4,481,365 | 11/1984 | Forster et al. | 556/422 |
| 4,663,314 | 5/1987 | Hayase et al. | 514/63 |
| 4,709,068 | 11/1987 | Sieburth | 556/447 |

FOREIGN PATENT DOCUMENTS

| | | | |
|---|---|---|---|
| 7371287 | 5/1987 | Australia | 546/14 |
| 60-123491 | 7/1985 | Japan | 556/447 |
| 61-87687 | 5/1986 | Japan | 556/447 |
| 2120664 B | 7/1986 | United Kingdom | 556/447 |

Primary Examiner—Robert T. Bond
Attorney, Agent, or Firm—Curtis, Morris & Safford

[57] ABSTRACT

The compounds of the formula (I)

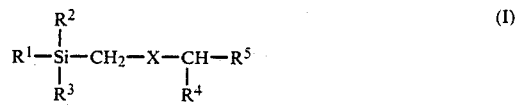

in which
X denotes $CH_2$ or O,
$R^1$ denotes (subst.) pyridyl or (subst.) pyrimidyl,
$R^2$ and $R^3$ denote alkyl or alkenyl or $R^2$ and $R^3$ denote an alkylene chain,
$R^4$ denotes —H, —CN, —$CCl_3$, —C≡CH, alkyl, F, or —C(S)—$NH_2$,
$R^5$ denotes pyridyl, furyl, thienyl, phthalimidyl, di($C_1$-$C_4$)alkylmaleimidyl, thiophthalimidyl, dihydrophthalimidyl or tetrahydrophthalimidyl, which may all be substituted, or substituted phenyl, or
$R^4$ and $R^5$—together with the carbon atom bridging them—denote an optionally substituted indanyl, cyclopentenoyl or cyclopentenyl radical, have advantageous insecticidal, acaricidal and nematocidal properties.

8 Claims, No Drawings

SILANE DERIVATIVES, AGENTS CONTAINING THEM, AND THEIR USE AS PESTICIDES

The basic structures known hitherto of insecticidal, acaricidal and nematocidal active compounds include such differing groups of substances as, for example, the phosphoric acid derivatives, the chlorohydrocarbons, the N-methylcarbamates, the cyclopropanecarboxylates and the benzoylureas, to mention just a few of the most important. Amazingly, however, (with a single exception, see Japanese Published Specification No. 60/123,491) no insecticidal, acaricidal and nematocidal compounds which contain a basic structure containing the element silicon have hitherto been described (C. Worthing, The Pesticide Manual, 7th edition, Lavenham 1983; S. Pawlenko, Organo-Silicium-Verbindungen [Organosilicon Compounds] in: Methoden der org. Chemie [Methods of Organic Chemistry] (Houben-Weyl), Volume XIII/5, Georg Thieme Verlag, Stuttgart 1980; R. Wegler, Chemie der Pflanzenschutz- und Schädlingsbekämpfungsmittel [The Chemistry of Plant-Protection Agents and Pesticides], Vols. 1, 6 and 7, Springer-Verlag, Berlin 1970, 1981). The same fact applies to the herbicide sector, and fungicide research has also only led to one case hitherto of the discovery of a silicon-containing basic structure for triazole fungicides (EP-A No. 68,813).

Novel active compounds having a silicon-containing basic structure have now been found which have advantageous applicational properties in the area of the insecticides, acaricides and nematocides.

The present invention thus relates to the compounds of the formula (I), the various optical isomers, and the possible mixtures of these, $$R^1-\underset{\underset{R^3}{|}}{\overset{\overset{R^2}{|}}{Si}}-CH_2-X-\underset{\underset{R^4}{|}}{CH}-R^5 \quad (I)$$

in which

X denotes $CH_2$ or O, $R^1$ denotes unsubstituted or substituted pyridyl or unsubstituted or substituted pyrimidyl, $R^2$ and $R^3$ denote $(C_1-C_3)$alkyl or $(C_2-C_8)$alkenyl, or $R^2$ and $R^3$ denote an alkylene chain which—together with the silicon atom—produces an unsubstituted or $(C_1-C_4)$alkyl-substituted heterocycle having four to six ring members, $R^4$ denotes —H, —CN, —$CCl_3$, —C≡CH, $(C_1-C_4)$alkyl, F or

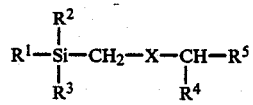

and $R^5$ denotes pyridyl, furyl, thienyl, phthalimidyl, di(C$_1$-C$_4$)alkylmaleimidyl, thiophthalimidyl, dihydrophthalimidyl, tetrahydrophthalimidyl, which can all be substituted, or substituted phenyl or $R^4$ and $R^5$—together with the carbon atoms bridging them—denote an optionally substituted indanyl, cyclopentanoyl or cyclopentenyl radical.

Optionally substituted pyridyl $R^1$ or pyrimidyl $R^1$ is preferably a pyridyl or pyrimidyl radical of the general formula (A) or (B),

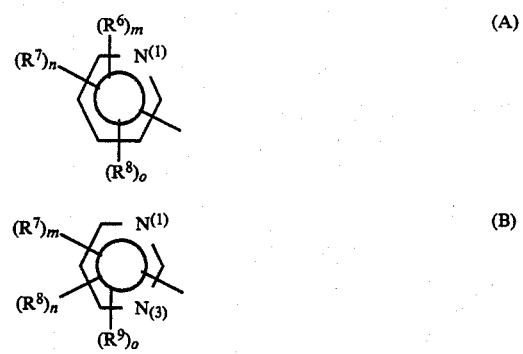

in which $0 \leq m+n+o \leq 3$ and m, n and o can have the vaues 0 to 2. $R^6$, $R^7$, $R^8$, and $R^9$ independently of one another, represent halogen, $(C_1-C_4)$alkyl, $(C_1-C_3)$alkoxy, $(C_1-C_3)$haloalkyl or $(C_1-C_3)$haloalkoxy or two of the radicals $R^6$, $R^7$, $R^8$ and $R^9$, if they are in the ortho-positions to one another, form a methylenedioxy, ethylenedioxy or $(C_3-C_5)$-alkylene radical.

The linking point (free valence) of the pyridyl radical (for example in formula A) on the Si atom in formula I is preferably in the 2 or 3 position of the pyridyl radical (N=position 1). The pyrimidyl radical (for example formula B) is preferably bound to the Si atom in position 2 or 5. Monosubstituted or disubstituted pyridyl or pyrimidyl radicals, in particular of the formula (A) or (B) where m+n+o=1 or 2, the substituents ($R_6$-$R_9$) being oriented, in particular, in the para or meta position to the linking point (Si atom), are preferred.

$R^2$ and $R^3$ preferably represent a $(C_1-C_3)$alkyl radical such as methyl, ethyl, i-propyl or n-propyl, or $R^2$ and $R^3$ form a $(C_3-C_5)$alkylene chain which—together with the silicon atom—produces a four-to six-membered ring such as, for example, silacylobutane, silacyclopentane or silacyclohexane.

$R^2$ and $R^3$ particularly preferably represent methyl.

$R^4$ preferably represents hydrogen, cyano or $(C_1-C_4)$alkyl, but particularly preferably hydrogen.

In particular, $R^6$-$R^9$ represent F, Cl, Br, methyl, ethyl, propyl, methoxy, ethoxy, propoxy, i-propoxy, difluoromethoxy, trifluoromethoxy, 1,1,2,2-tetrafluoroethoxy, 2,2,2-trifluoroethoxy, 1,1,2,3,3,3-hexafluoropropoxy, 1,1,2-trifluoro-2-chloroethoxy, trifluoromethyl, 1,1,2,2-tetrafluoroethyl, heptafluoropropyl, methylenedioxy and ethylenedioxy.

As substituted phenyl, $R^5$ is preferably a phenyl radical of the general formula (C),

in which $R^{10}$ and $R^{11}$—independently of one another—may denote halogen, $(C_1-C_4)$alkyl, $(C_1-C_4)$alkoxy, $(C_1-C_4)$haloalkyl, phenyl, N-pyrrolyl or a group of the general formula (D)

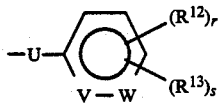 (D)

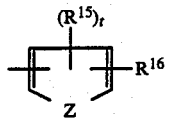 (F)

in which

R$^{12}$ and R$^{13}$—independently of one another—may denote H, halogen, (C$_1$–C$_4$)alkyl, (C$_1$–C$_4$)alkoxy or (C$_1$–C$_4$)haloalkyl, U denotes —CH$_2$—,

—O— or —S—, but preferably —O—;

V and W denote CH or N, where both may simulaneously denote CH but cannot simultaneously denote N, and where, in the formulae (C) and (D)

p and q denote an integer from 0 to 5, with the condition that the sum p+q must denote a number from 1 to 5, r and s denote 0, 1 or 2, with the condition that the sum of r+s must be 0, 1 or 2, and with the condition that, if R$^{10}$ or R$^{11}$ corresponds to the group (D), p and q must denote 0 or 1 and p+q must denote 1 or 2.

Of these radicals for R$^5$, radicals of the formula (C) in which (R$^{10}$)$_p$ denotes H or 4-fluoro, and (R$^{11}$)$_q$ is located in the 3-position of the phenyl radical and denotes the radical

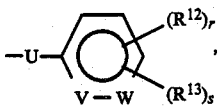

where r+s preferably represents O, are of particular importance.

As optionally substituted pyridyl, R$^5$ represents a monosubstituted pyridyl group of the general formula (E),

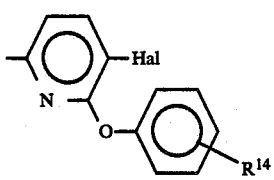 (E)

in which

R$^{14}$ denotes halogen, apart from I, (C$_1$–C$_4$)alkyl, (C$_1$–C$_4$)alkoxy or (C$_1$–C$_4$)haloalkyl and Hal denotes halogen, particularly fluorine, or H.

R$^5$ in optionally substituted thienyl or furyl represents a heterocycle of the general formula (F), in which Z denotes O or S, R$^{15}$ denotes H, halogen, (C$_1$–C$_4$)alkyl, (C$_1$–C$_4$)alkoxy, (C$_1$–C$_4$)haloalkyl, CN or NO$_2$, and R$^{16}$ denotes optionally substituted benzyl, propargyl, allyl or phenoxy.

Substituted phenyl radicals for R$^5$ are of particular importance for the invention.

The following radicals are specified as typical examples of the group R$^5$:

pentafluorophenyl, 5-benzyl-3-furyl, 4-phenoxyphenyl, 3-phenoxyphenyl, 3-(4-fluorophenoxy)phenyl, 3-(4-chlorophenoxy)phenyl, 3-(4-bromophenoxy)phenyl, 3-(3-fluorophenoxy)phenyl, 3-(3-chlorophenoxy)phenyl, 3-(3-bromophenoxy)phenyl, 3-(2-fluorophenoxy)phenyl, 3-(2-chlorophenoxy)phenyl, 3-(2-bromophenoxy)phenyl, 3-(4-methylphenoxy)phenyl, 3-(3-methylphenoxy)phenyl, 3-(2-methylphenoxy)phenyl, 3-(4-methoxyphenoxy)phenyl, 3-(3-methoxyphenoxy)phenyl, 3-(2-methoxyphenoxy)phenyl, 3-(4-ethoxyphenoxy)phenyl, 3-(phenylthio)phenyl, 3-(4-fluorophenylthio)phenyl, 3-(3-fluorophenylthio)phenyl, 3-benzoylphenyl, 3-benzylphenyl, 3-(4-fluorobenzyl)phenyl, 3-(4-chlorobenzyl)phenyl, 3-(3,5-dichlorophenoxy)phenyl, 3-(3,4-dichlorophenoxy)phenyl, 3-(4-chloro-2-methylphenoxy)phenyl, 3-(2-chloro-5-methylphenoxy)phenyl, 3-(4-chloro-5-methylphenoxy)phenyl, 3-(4-ethylphenoxy)phenyl, 3-(3-chloro-5-methoxyphenoxy)phenyl, 3-(2,5-dichlorophenoxy)phenyl, 3-(3,5-dichlorobenzoyl)phenyl, 3-(3,4-dichlorobenzoyl)phenyl, 3-(4-methylbenzyl)phenyl, 3-(4-isopropoxyphenoxy)phenyl, 4-fluoro-3-phenoxyphenyl, 4-chloro-3-phenoxyphenyl, 4-bromo-3-phenoxyphenyl, 4-fluoro-3-(4-fluorophenoxy)phenyl, 4-fluoro-3-(4-chlorophenoxy)phenyl, 4-fluoro-3-(4-bromophenoxy)phenyl, 4-fluoro-3-(4-methylphenoxy)phenyl, 4-fluoro-3-(4-methoxyphenyl)phenyl, 4-fluoro-3-(3-fluorophenoxy)phenyl, 4-fluoro-3-(3-chlorophenoxy)phenyl, 4-fluoro-3-(3-bromophenoxy)phenyl, 4-fluoro-3-(3-methoxyphenoxy)phenyl, 4-fluoro-3-(4-ethoxyphenoxy)phenyl, 4-fluoro-3-(2-fluorophenoxy)phenyl, 3-methoxy-5-phenoxyphenyl, 2-fluoro-3-phenoxyphenyl, 2-fluoro-3-(4-fluorophenoxy)phenyl, 2-fluoro-3-(3-fluorophenoxy)phenyl, 2-fluoro-3-(2-fluorophenoxy)phenyl, 3-fluoro-5-(4-fluorophenoxy)phenyl, 3-fluoro-5-(3-fluorophenoxy)phenyl, 3-fluoro-5-(2-fluorophenoxy)phenyl, 4-methyl-3-phenoxy-phenyl, 3-fluoro-5-(4-methylphenoxy)phenyl, 3-fluoro-5-(3-methoxyphenoxy)phenyl, 2-fluoro-5-(4-fluorophenoxy)phenyl, 2-fluoro-5-(3-fluorophenoxy)phenyl, 2-fluoro-5-(2-fluorophenoxy)phenyl, 2-chloro-3-phenoxyphenyl, 3-fluoro-5-phenoxyphenyl, 2-fluoro-5-phenoxyphenyl, 2-chloro-5-phenoxyphenyl, 2-bromo-5-phenoxyphenyl, 4-chloro-3-(3-methylphenoxy)phenyl, 4-chloro-3-(4-fluorophenoxy)-phenyl, 3-chloro-5-phenoxyphenyl, 3-bromo-5-phenoxyphenyl, 4-bromo-3-phenoxyphenyl, 4-trifluoromethyl-3-phenoxyphenyl, 4-fluoro-3-phenylthiophenyl, 4-fluoro-3-benzylphenyl, 3-(2-pyridyloxy)phenyl, 3-(3-pyridyloxy)phenyl, 4-fluoro-3-(2-pyridyloxy)phenyl, 4-chloro-3-(2-pyridyloxy)phenyl, 4-bromo-3-(2-pyridyloxy)phenyl, 4-methyl-3-(2-pyridyloxy)-phenyl, 4-fluoro-3-(3-pyridyloxy)phenyl, 4-chloro-3-(3-pyridyloxy)phenyl, 4-bromo-3-(3-pyridyloxy)phenyl, 4-methyl-3-(3-pyridyloxyphenyl), 2-methyl-3-phenylphenyl, 2-methyl-3-(N-pyrrolyl)phenyl, 6-phenoxy-2-pyridyl, 6-(4-fluorophenoxy)-2-pyridyl, 6-(4-chlorophenoxy)-2-pyridyl, 6-(4-bromophenoxy)-2-pyridyl, 6-(4-methylphenoxy)-2-pyridyl, 6-(4-methoxyphenoxy)-2-pyridyl, 6-(4-ethoxyphenoxy)-2-pyridyl, 6-(3-fluorophenoxy)-2-pyridyl, 6-(3-chlorophenoxy)-2-pyridyl, 6-(3-bromophenoxy)-2-pyridyl, 6-(3-methoxyphenoxy)-2-pyridyl, 6-(2-fluorophenoxy)-2-pyridyl, 6-(2-chlorophenoxy)-2-pyridyl, 6-(2-bromophenoxy)-2-pyridyl, 5-propargyl-3-furyl, N-phthalimidyl, N-3,4,5,6-phthalimidyl, 2-methyl-5-propargyl-3-furyl, 4-t-butylphenyl, 4-methylphenyl, 4-isopropylphenyl, 4-(2-chloro-4-trifluoromethyl-2-pyridyloxy)phenyl, 4-cyclohexylphenyl, 4-difluoromethoxyphenyl, 4-biphenylyl, 4-trimethylsilylphenyl and 4-phenoxy-2-thienyl.

Further typical examples of the group

are:

2-allyl-3-methylcyclopent-2-en-1-on-4-yl and 4-phenylindan-2-yl.

The present invention also relates to processes for the preparation of the compounds of the general formula (I) wherein (a) for compounds having $X=CH_2$, a silane of the general formula (II),

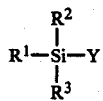     (II)

in which
Y denotes a nucleofugic leaving group such as, for example, halogen or sulfonate, is reacted with an organometallic reagent of the general formula (III),

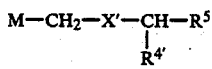     (III)

in which
M corresponds to an alkali metal or alkaline earth metal equivalent, particularly Li, Na, K, or Mg,
X' corresponds to a methylene group, and
$R^{4'}$ corresponds to H or $(C_1-C_4)$alkyl, or (b) a silane of the general formula (IV) or (V)

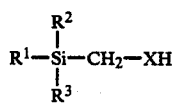     (IV)

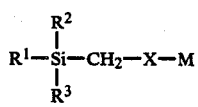     (V)

is reacted with an alkylating agent of the general formula (VI)

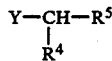     (VI)

if appropriate in the presence of a base, or
(c) a silane of the general formula (VII)

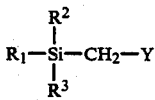     (VII)

is reacted with a XH-acidic compound of the type (VIII)

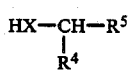     (VIII)

in the presence of a base, or with an organometallic compound of the type (IX)

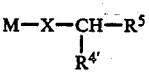     (IX)

or
(d) for compound where $X=CH_2$, a silane of the general formula (X)

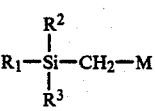     (X)

is reacted with a compound of the type (XI)

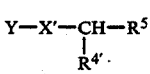     (XI)

or
(e) for compounds where $X=CH_2$, a silane of the general formula (XII)

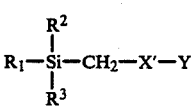     (XII)

is reacted with an organometallic compound of the general formula (XIII)

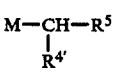     (XIII)

or
(f) a silane of the general formula (XIV)

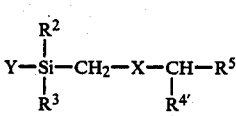     (XIV)

is reacted with an organometallic reagent of the type (XV)

$$R^1-M \quad (XV)$$

or (g) a silane of the general formula (XVI)

$$R^1-\underset{\underset{R^3}{|}}{\overset{\overset{R^2}{|}}{Si}}-CH_2-X-\underset{\underset{R^4}{|}}{CH}-Y \quad (XVI)$$

is reacted with an organometallic reagent of the type (XVII)

$$M-R^5 \quad (XVII)$$

if appropriate in the presence of a transition metal catalyst of the auxiliary group I or VIII of the periodic system such as CuBr or NiCl$_2$ or (h) for compounds where X=CH$_2$, a silane of the general formula (XXX)

$$R^1-\underset{\underset{R^3}{|}}{\overset{\overset{R^2}{|}}{Si}}-H \quad (XXX)$$

is reacted with an olefine of the general formula (XXXI)

$$H_2C=CH-\underset{\underset{R^4}{|}}{CH}-R^5$$

in the presence of a complex of an element of subgroup VIII of the periodic system as catalyst or (i) for compounds where X≠CH$_2$, a silane of the general formula (XXXII)

$$R^1-\underset{\underset{R^3}{|}}{\overset{\overset{R^2}{|}}{Si}}-M \quad (XXXII)$$

is reacted with an alkylating agent of the general formula (XXXIII)

$$Y-CH_2-X-\underset{\underset{R^{4'}}{|}}{CH}-R^5 \quad (XXXIII)$$

Some of the silanes of the formula (II) to be used as starting compounds in the preparation process (a) are novel and can be prepared, by a process which is known per se from the literature, by starting from a silane of the general formula (XVIII), (XIX) or (XX) and introducing the organic radicals which are still absent using suitable organometallic reagents (see Methoden der org. Chemie [Methods of Organic Chemistry] (Houben-Weyl), Vol. XIII/5, Georg Thieme Verlag, Stuttgart, 1980), $$Y_4Si + R-M \longrightarrow Y_3Si-R$$
$$(XVIII) \quad\quad\quad\quad (XIX)$$

$$Y_3SiR + R'M \longrightarrow R'Si(Y)_2R$$
$$(XIX) \quad\quad\quad\quad (XX)$$

$$R'Si(Y)_2R + R''M \longrightarrow R'-\underset{\underset{R''}{|}}{\overset{\overset{R}{|}}{Si}}-Y$$
$$(XX) \quad\quad\quad\quad\quad\quad (II)$$

in which

R, R' and R'' correspond to the radicals R$^1$, R$^2$ and R$^3$, and Y and M are as defined above.

Some of the organometallic reagents of the general formula (III) to be used as starting compounds in the preparation process (a) are novel and can be prepared, by processes which are known per se from the literature, by initially converting a carbonyl compound of the general formula (XXI), $$O=C\underset{R^4}{\overset{R^5}{<}} \quad (XXI)$$

in which

R$^4$ and R$^5$ are as defined above, according to Reformatskij (see Methoden der org. Chemie [Methods of Organic Chemistry](Houben-Weyl), Vol. XIII/2a, Georg Thieme Verlag, Stuttgart 1973), according to Wittig (see Methoden der org. Chemie [Methods of Organic Chemistry[ (Houben-Weyl), Vol. E1, Georg Thieme Verlag, Stuttgart 1982) or according to Horner (see L. Horner, Fortschr. Chem. Forsch. 7/1, 1 (1966/67)) to the corresponding α,β-unsaturated ester (XXII), $$RO_2C-CH=C\underset{R^4}{\overset{R^5}{<}} \quad (XXII)$$

then reducing this by standard methods (see Methoden der org. Chemie [Methods of Organic Chemistry] (Houben-Weyl), Vol. 4/1c and 4/1d, Georg Thieme Verlag, Stuttgart 1980 and 1981) to the alcohol (XXIII), $$HO-CH_2-CH_2-CH\underset{R^4}{\overset{R^5}{<}} \quad (XXIII)$$

and then converting this by standard methods (see Methoden der org. Chemie [Methods of Organic Chemistry] (Houben-Weyl), Vol. 5/3 and 5/4, Georg Thieme Verlag, Stuttgart, 1960 and 1962) to a suitable halide (XXIV), $$Hal-CH_2-CH_2-CH\underset{R^4}{\overset{R^5}{<}} \quad (XXIV)$$

which finally reacts with an alkali metal or alkaline earth metal to give the required organometallic reagents of the type (III).

Some of the silanes of the general formula (IV) and (V) to be used as starting compounds in the preparation process (b) are novel and can be prepared, by methods which are known per se from the literature (see Methoden der org. Chemie [Methods of Organic Chemistry] (Houben-Weyl), Vol. XIII/5, Georg Thieme Verlag, Stuttgart 1980), by (1) reacting a silane of the general formula (XXV),

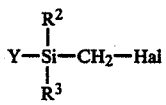
(XXV)

in which
R$^2$, R$^3$ and Y are as defined above and Hal can be Br or Cl, with an organometallic reagent of the general formula (XV),

R$^1$—M  (XV)

then converting the intermediate of the type (VII)

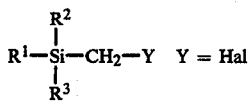
(VII)

by standard methods (see Methoden der org. Chemie [Methods of Organic Chemistry] (Houben-Weyl), Vol. 13/3a, Georg Thieme Belarg, Stuttgart, 1982) to the borane (XXVI),

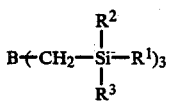
(XXVI)

and finally cleaving this, by methods which are known from the literature (see Methoden der org. Chemie [Methods of Organic Chemistry] (Houben-Weyl), Vol. 13/3c, Georg Thieme Verlag, Stuttgart 1984), to form the desired compounds (IV) (X=O or S).

(2) converting a silane of the general formula (XXVII),

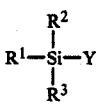
(XXVII)

in which
Y denotes halogen or

by methods which are known from the literature (see Methoden der org. Chemie [Methods of Organic Chemistry] (Houben-Weyl), Vol. XIII/5, Georg Thieme Verlag, Stuttgart, 1980) to the corresponding metallated silane using an alkali metal, and then reacting with formaldehyde, compounds of the type (IV) having X=O being obtained.

(3) reacting a silane of the general formula (XXVIII),

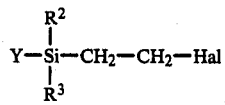
(XXVIII)

in which
R$^2$, R$^3$ and Y are as defined above and Hal denotes Cl or Br, with an organometallic reagent of the formula (XV)

R$^1$—M  (XV)

and reacting the intermediate (XXIX) produced

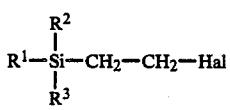
(XXIX)

with an alkali metal or alkaline earth metal, compounds of the type (V) having X=CH$_2$ being obtained.

The silanes of the general formula (VII)

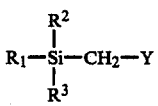
(VII)

to be used as starting compounds in the preparation process (c) can be produced —for Y=Hal—as described above by reaction of the silanes (XXV) with organometallic reagents (XV).

The compounds (VII) having Y=sulfonate can expediently be synthesized by esterification of the alcohols of the type (IV),

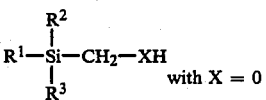
(IV)

having sulfonic acid radicals, by conventional methods (see Methoden der org. Chemie [Methods of Organic Chemistry] (Houben-Weyl), Vol. IX, Georg Thieme Verlag, Stuttgart, 1955).

Some of the silanes of the general formula (XXX) to be used as starting compounds in the preparation process (h) are novel and can be prepared by methods which are known per se from the literature (see Methoden der org. Chemie [Methods of Organic Chemistry] (Houben-Weyl), Vol. XIII/5, Georg Thieme Verlag, Stuttgart, 1980), by (1) reacting a silane of the general formula (XXXIV)

(XXXIV)

with an organometallic reagent of the formula (XI)

$$R^1\text{—}M \quad (XI)$$

or (2) reducing a silane of the general formula II $$R^1\text{—}\underset{\underset{R^3}{|}}{\overset{\overset{R^2}{|}}{Si}}\text{—}Y \quad (II)$$

using metal hydrides such as, for example, sodium hydride or lithium aluminum hydride.

The olefines of the general formula (XXXI)

$$H_2C\text{=}CH\text{—}\underset{\underset{R^4}{|}}{CH}\text{—}R^5 \quad (XXXI)$$

to be used as starting compounds in the preparation process (h) can be prepared by methods which are known per se from the literature, by reacting an olefine of the general formula (XXXVa) or (XXXVb)

$$H_2C\text{=}CH\text{—}\underset{\underset{R^4}{|}}{CH}\text{—}Y \quad (XXXVa)$$

$$H_2C\text{=}CH\text{—}\underset{\underset{R^5}{|}}{CH}\text{—}Y \quad (XXXVb)$$

with an organometallic reagent, of the general formula (XXXVIa) or (XXXVIb)

$$M\text{—}R^5 \quad (XXXVIa)$$
$$M\text{—}R^{4'} \quad (XXXVIb)$$

which can be obtained from the corresponding halogen compound.

Some of the compounds of the formula (XXXI) are novel.

The present invention therefore also relates to compounds of the formula (XXXI) in which
$R^4$ denotes H and
$R^5$ denotes a radical of the formulae

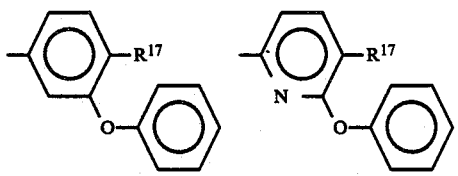

or

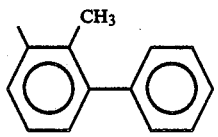

$R^{17}$ represents H or halogen, where halogen particularly denotes fluorine.

Some of the metallated silanes of the general formula (XXXII)

$$R^1\text{—}\underset{\underset{R^3}{|}}{\overset{\overset{R^2}{|}}{Si}}\text{—}M \quad (XXXII)$$

to be used as starting compounds in the preparation process (i) are novel and can be prepared, by methods which are known from the literature, from the educts (XXVII)

$$R^1\text{—}\underset{\underset{R^3}{|}}{\overset{\overset{R^2}{|}}{Si}}\text{—}Y' \quad (XXVII)$$

in which
Y' denotes Hal or $$-\underset{\underset{R^3}{|}}{\overset{\overset{R^2}{|}}{Si}}\text{—}R^1,$$

by reaction with an alkali metal.

Some of the alkylating agents (XXXIII)

$$Y\text{—}CH_2\text{—}X\text{—}\underset{\underset{R^4}{|}}{CH}\text{—}R^5; \ X \neq CH_2 \quad (XXXIII)$$

to be used as starting compounds in the preparation process (i) are also novel and can be prepared by methods which are known from the literature (see, for example, Methoden der org. Chemie [Methods of Organic Chemistry] (Houben-Weyl), Vol. V/3, Georg Thieme Verlag, Stuttgart, 1962), for example, for X=O, by reacting an alcohol of the general formula (XXXVII)

$$HO\text{—}\underset{\underset{R^4}{|}}{CH}\text{—}R^5 \quad (XXXVII)$$

with a halogenating agent such as, for example, hydrochloric acid, hydrobromic acid or thionyl chloride, in the presence of paraformaldehyde.

Some of the further compounds of the general formulae (VI), (VIII), (IX), (X), (XI), (XII), (XIII), (XIV), (XV), (XVI) and (XVII) to be used as starting compounds are novel. They are synthesized by the synthesis stages cited in the text above (see the literature cited above), or by standard methods of organic chemistry. Thus, the organometallic intermediates can be produced, for example, by hydrogen/metal exchange or —preferably—by halogen/metal exchange in all its variants.

The process versions (a), (d), (e), (f), (g) and (i) mentioned are preferably carried out in a diluent whose nature depends on the type of the organometallic compound employed. Suitable diluents are, in particular, aliphatic and aromatic hydrocarbons such as, for example, pentane, hexane, heptane, cyclohexane, petroleum ether, benzine, ligroine, benzene, toluene and xylene, ethers such as, for example, diethyl and dibutyl ether, glycol dimethyl ether, diglycol dimethyl ether, tetrahydrofuran and dioxane, and finally all possible mixtures of the abovementioned solvents.

The reaction temperature in the abovementioned process versions is between −75° C. and +150° C., preferably between −75° C. and +105° C. The starting materials are usually employed in equimolar amounts. However, an excess of one or other of the reaction components is possible.

The same is essentially valid for the abovementioned process versions (b) and (c) as for versions (a) and (d)–(g). When educts of the type (IV) and (VIII) are used, however, further diluents can be employed. Thus, in these cases, ketones such as acetone, methylethyl ketone, methylisopropyl ketone and methyl isobutyl ketone, esters such as methyl and ethyl acetate, nitriles such as, for example, acetonitrile and propionitrile, amides such as, for example, dimethylformamide, dimethylacetamide and N-methylpyrrolidone, and dimethyl sulfoxide, tetramethylene sulfone and hexamethylphosphoric triamide are also suitable as diluents. Inorganic bases such as, for example, alkali metal or alkaline earth metal hydroxides, hydrides, carbonates or bicarbonates, but also organic bases such as, for example, pyridine, triethylamine, N,N-diisopropylethylamine or diazabicyclooctane are used as bases.

The process version (h) mentioned is preferably carried out—in contrast to all other processes for the synthesis of compounds of the general formula I—without diluent. However, solvents such as cyclohexane, petroleum ether, benzene, toluene, tylol and others are also suitable as reaction medium. Complex compounds of the elements of subgroup VIII of the periodic system, such as, for example, $H_2PtCl_6$, $Co_2(CO)_8$, $Rh_4(CO)_{12}$, $Ir_4(CO)_{12}$, or $RhCl[P(C_6H_5)_3]_3$ are used as catalysts (see Methoden der org. Chemie [Methods of Organic Chemistry] (Houben-Weyl), Vol. XIII/5, Georg Thieme Verlag, Stuttgart, 1980, p. 51 et. seq. and the literature cited therein). The catalyst to reacted educts ratio depends on the type of the catalyst and, in the case of $H_2PtCl_6$, for example, varies in the range $1:10^7$ to $1:10^6$.

The compounds of the formula (I) are isolated and, if appropriate, purified by generally conventional methods, for example by evaporation of the solvent (if appropriate under reduced pressure) and subsequent distillation or chromatography, or by distribution of the crude product between two phases and subsequent conventional work-up.

The compounds of the general formula (I) are easily soluble in most organic solvents.

The active compounds are suitable for combating animal pests, in particular insects, arachnida and nematodes, encountered in agriculture, in forestry, in the protection of stored products and of materials, and in the hygiene field, and have good plant tolerance and favorable toxicity to warm-blooded animals. They are active against normally sensitive and resistant species and against all or some stages of development. The abovementioned pests include:

From the order of the Isopoda, for example, *Oniscus asellus, Armadillidium vulgare* and *Porcellio scaber.* From the order of the Diplopoda, for example, *Blaniulus guttulatus.* From the order of the Chilopoda, for example, *Geophilus carpophagus* and Scutigera spec. From the order of the Symphyla, for example, *Scutigerella immaculata.* From the order of the Thysanura, for example, *Lepisma saccharina.* From the order of the Collembola, for example, *Onychiurus armatus.* From the order of the Orthoptera, for example, *Blatta orientalis, Periplaneta americana, Leucophaea maderae, Blattella germanica, Acheta domesticus,* Gryllotalpa spp., *Locusta migratoria migratorioides,* Melanoplus differentialis and *Schistocerca gregaria.* From the order of the Dermaptera, for example, *Forficula auricularia.* From the order of the Isoptera, for example, Reticulitermes spp. From the order of the Anoplura, for example, *Phylloxera vastatrix,* Phemphigus spp., *Pediculus humanus corporis,* Haematopinus spp. and Lignognathus spp. From the order of the Mallophaga, for example, Trichodectes spp. and Damalinea spp. From the order of the Thysanoptera, for example, *Hercinothrips femoralis* and *Thrips tabaci.* From the order of the Heteroptera, for example, Eurygaster spp., *Dysdercus intermedius, Piesma quadrata, Cimex lectularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Naphotettix cincticeps, Lecanium corni, Saissetia oleae, Laodelphax striatellus, Nilaparvata lugens, Aonidiella aurantii, Aspidiotus hederae,* Pseudococcus spp. and Psylla spp. From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp. *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia koehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.* From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamenis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.* From the order of the Hymenoptera, for example, Diprion spp., Hoplocampa spp., Lasius spp., *Monomorium pharaonis* and Vespa spp. From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., Bibio hortulanus, Oscinella frit, Phorbia spp., *Pegomyia hyoscyami, Ceratitis capitata, Dacus oleae* and *Tipula paludosa.* From the order of the Siphonaptera, for example, *Xenopsylla cheopis* and Ceratophyllus spp. From the order of the Arachnida, for example, *Scorpio maurus* and *Latrodectus mactans.* From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp. and Tetranychus spp.

The compounds furthermore have an excellent action against nematodes which are harmful to plants, for example against those of the genera Meloidogyne, Heterodera, Ditylenchus Aphelenchoides, Radopholus, Globodera, Pratylenchus, Longidorus and Xiphinema.

The invention also relates to agents which contain the compounds of the formula (I) in addition to suitable formulation auxiliaries.

The agents according to the invention contain the active compounds of the formula (I), in general to 1–95% of weight. They can be used in the conventional preparations as wettable powders, emulsifiable concentrates, sprayable solutions, dusting agents or granulates.

Wettable powders are preparations which can be dispersed uniformly in water and which also contain, besides the active compound and a diluent or inert substance, wetting agents, for example polyoxethylated alkylphenols, polyoxethylated fatty alcohols or alkyl or alkylphenol sulfonates, and dispersing agents, for example sodium ligninsulfonate, sodium, 2,2'-dinaphthylmethane-6,6'-disulfonate, sodium dibutylnaphthalenesulfonate or sodium oleylmethyltaurate.

Emulsifiable concentrates are prepared by dissolving the active compound in an organic solvent, for example butanol, cyclohexanone, dimethylformamide, xylene or, alternatively, higher boiling aromatics or hydrocarbons, with addition of one or more emulsifiers. Examples of emulsifiers which may be used are: calcium salts of alkylarylsulfonic acid, such as calcium dodecylbenzenesulfonate, or nonionic emulsifiers such as fatty acid polyglycol esters, alkylaryl polyglycol ethers, fatty alcohol polyglycol ethers, propylene oxide/ethylene oxide condensation products, alkyl polyethers, sorbitan fatty acid esters, polyoxyethylene sorbitan fatty acid esters or polyoxyethylene sorbitol esters.

Dusting agents are obtained by grinding the active compound with finely divided solid substances, for example talc, natural clays such as kaolin, bentonite, poryphillite or diatomaceous earth. Granules can be prepared either by atomizing the active compound onto adsorptive, granulated inert material or by applying the active compound concentrates by means of adhesives, for example polyvinyl alcohol, sodium polyacrylate or, alternatively, mineral oils, onto the surface of carrier materials such as sand, kaolinites or granulated inert material. Suitable active compounds can also be prepared in the conventional fashion for the preparation of fertilizer granulates—if desired as a mixture with fertilizers.

The active compounds according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example phosphates, carbamates, carboxylates, formamidines, tin compounds and substances produced by microorganisms, inter alia. Preferred co-constituents of the mixture are 1. from the group comprising the phosphates, azinphosethyl, azinphos-methyl, 1-(4-chlorophenyl)-4-(O-ethyl, S-propyl)phosphoryloxypyrazole (TIA-230), chlorpyrifos, coumaphos, demeton, demeton-S-methyl, diazinon, dichlorvos, dimethoat, ethoprophos, etrimfos, fenitrothion, fenthion, heptenophos, parathion, parathionmethyl, phosalon, pirimiphos-ethyl, pirimiphos-methyl, profenofos, prothiofos, sulprofos, triazophos, trichlorphon.

2. from the group comprising the carbamates, aldicarb, bendiocarb, BPMC (2-(1-Methylpropyl)phenylmethylcarbamate), butocarboxim, butoxicarboxim, carbaryl, carbofuran, carbosulfan, cloethocarb, isoprocarb, methomyl, oxamyl, primicarb, promecarb, propoxur, thiodicarb.

3. from the group comprising the carboxylates, allethrin, alphametrin, bioallethrin, bioresmethrin, cycloprothrin, cyfluthrin, cyhalothrin, cypermethrin, deltamethrin, α-cyano-3-phenyl-2-methylbenzyl 2,2-dimethyl-3-(2-chloro-2-trifluoromethylvinyl)cyclopropanoate (FMC 54800), fenpropathrin, fenfluthrin, fenvalerat, flucythrinate, flumethrin, fluvalinate, permethrin, resmethrin, tralomethrin.

4. from the group comprising the formamidines, amitraz, chlordimeform 5. from the group comprising the tin compounds, azocyclotin, cyhexatin, fenbutatin-oxid 6. others α- and β-avermectins, *Bacillus thuringiensis*, bensultap, binapacryl, bisclofentezin, buprofecin, cartrap, cyromacin, dicofol, endosulfan, ethoproxyfen, fenoxycarb, hexythiazox, 3-[2-(4-ethoxyphenyl)-2-methylpropoxymethyl]-1,3-diphenyl ether (MTI-500), 5-[4-(ethoxyphenyl)-4-methylpentyl]-2-fluoro-1,3-diphenyl ether (MTI-800), 3-(2-chlorophenyl)-3-hydroxy-2-(2-phenyl-4-thiazolyl)propene nitrile (SN 72129), thiocyclam, nuclear polyhedroses and granuloses of viruses.

The active compound concentration in the use forms prepared from the commercially available formulations can vary within wide ranges. The active compound concentration of the use forms can be between 0.0000001 to 100% by weight of active compound, preferably between 0.00001 and 1% by weight.

The application occurs in a conventional fashion which is matched to the use forms.

The active compounds according to the invention are also suitable for combating ecto- and endoparasites, preferably ectoparasitic insects, in the veterinary medicine field and in the field of animal husbandry.

The active compounds according to the invention are used here in a known fashion, such as by oral administration in the form of, for example, tablets, capsules, drenches or granulates, by dermal administration in the form of, for example, dipping, spraying, pouring-on, spotting-on and powdering.

The suitable dosages and formulations in each case are particularly dependent on the type and stage of development of the productive livestock and also on the infestation intensity of the insects, and can easily be determined and fixed by the conventional methods. In the case of cattle, the novel compounds may be employed, for example, in dosage amounts of 0.1 to 100 mg/kg of body weight.

The following examples illustrate the invention.

A. Formulation Examples (a) A dusting agent is obtained by mixing 10 parts by weight of active compound and 90 parts by weight of talc as inert substance and comminuting in an impact pulverizer.

(b) A wettable powder which can easily be dispersed in water is obtained by mixing 25 parts by weight of active compound, 65 parts by weight of kaolin-containing quartz as inert substance, 10 parts by weight of potassium ligninsulfonate and 1 part by weight of sodium oleoylmethyltaurate as wetting and dispersing agent, and grinding in a pin disc mill.

(c) A dispersion concentrate which can easily be dispersed in water is produced by mixing 20 parts by weight of active compound with 6 parts by weight of alkylphenol polyglycol ether (®Triton X 207), 3 parts by weight of isotridecanol polyglycol ether (8 EO) and 71 parts by weight of paraffinic mineral oil, (boiling range, for example, about 255 to above 377° C.), and ground to a fineness of below 5 microns in an abrasive ball mill.

(d) An emulsifiable concentrate can be produced from 15 parts by weight of active compound, 75 parts by weight of cyclohexanone as solvent and 10 parts by weight of oxethylated nonylphenol (10 EO) as emulsifier.

(e) A granulate can be produced from 2 to 15 parts by weight of active compound and an inert granulate support material such as attapulgite, pumice granulate and/or quartz sand.

B. Chemical Examples
Preparation procedure

A mixture of 18.2 g (0.09 mol) of 2-ethoxy-5-bromopyridine (can be obtained from 2,5-dibromopyridine and sodium methanolate in DMSO), 11.4 g (0.12 mol) of chlorodimethylsilane and 50 ml of anhydrous tetrahydrofuran (THF) is added dropwise to 2.4 g (0.10 mol) of magnesium turnings in 10 ml of anhydrous THF, a strongly exothermic reaction occurring. The reaction is completed by refluxing for two hours. The mixture is then poured into water and extracted repeatedly with n-hexane, The extracts are washed with water and saturated sodium chloride solution, dried and evaporated, and the residue is distilled. 7 g (43%) of 2-ethoxy-5-dimethylsilylpyridine are obtained as a colorless oil of boiling point 7=140°-150° C.

2 drops of a 30% strength solution of hexachloroplatinic acid in isopropanol are added to a mixture of 3.6 g (20 mmol) of 2-ethoxy-5-dimethylsilylpyridine and 4.2 g (20 mmol) of 3-allyldiphenyl ether. The exothermic reaction commences after gentle warming. The crude product obtained is subjected to bulb-tube distillation, and yields 3.6 g (46%) of (2-ethoxypyrid-5-yl)-dimethyl-<3-(3-phenoxyphenyl)propyl>silane as a colorless oil of boiling point 0.15=230° C.; $n_D^{20}$=1.5618

The compounds of the formula (I), where X=CH$_2$, listed below are prepared according to this procedure. The following compounds where X=O can be prepared, for example, by process (b) described on page 9. In each case in the table, et denotes ethyl.

$$R^1-\underset{\underset{R^3}{|}}{\overset{\overset{R^2}{|}}{Si}}-CH_2-X-\underset{\underset{R^4}{|}}{CH}-R^5$$

| Example No. | R$^1$ | R$^2$ | R$^3$ | X | R$^4$ | R$^5$ | Physical Data |
|---|---|---|---|---|---|---|---|
| 1 | 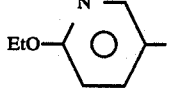 | CH$_3$ | CH$_3$ | CH$_2$ | H | 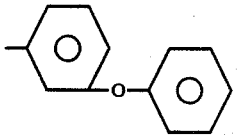 | b.p.$_{0.15}$ = 230° C. $n_D^{20}$ = 1.5618 |
| 2 | 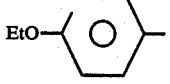 | CH$_3$ | CH$_3$ | CH$_2$ | H | 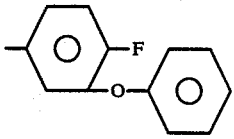 | b.p.$_{0.15}$ = 220° C. |
| 3 | 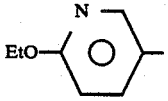 | CH$_3$ | CH$_3$ | CH$_2$ | H | 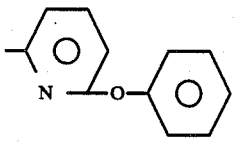 | b.p.$_{0.2}$ = 235° C. |
| 4 | 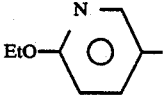 | CH$_3$ | CH$_3$ | CH$_2$ | H | 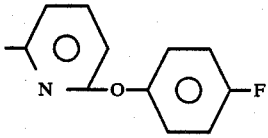 | |
| 5 | 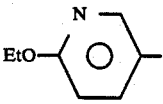 | CH$_3$ | CH$_3$ | CH$_2$ | H | 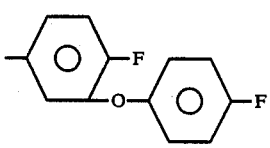 | b.p.$_{0.2}$ = 230° C. |

-continued $$R^1-\underset{\underset{R^3}{|}}{\overset{\overset{R^2}{|}}{Si}}-CH_2-X-CH-R^5 \atop {\phantom{Si-CH_2-X-C}|\atop \phantom{Si-CH_2-X-C}R^4}$$

| Example No. | R¹ | R² | R³ | X | R⁴ | R⁵ | Physical Data |
|---|---|---|---|---|---|---|---|
| 6 | 2-EtO-pyridin-5-yl | CH₃ | CH₃ | CH₂ | CN | 4-phenoxyphenyl | pale yellow oil; distils with decomposition |
| 7 | 2-EtO-pyridin-5-yl | CH₃ | CH₃ | CH₂ | H | 5-(phenoxy)thiophen-2-yl | |
| 8 | 2-EtO-pyridin-5-yl | CH₃ | CH₃ | O | H | 4-phenoxyphenyl | b.p.$_{0.1}$ = 230–235° C. |
| 9 | 2-EtO-pyridin-5-yl | CH₃ | CH₃ | O | H | 4-(phenoxy)-3-fluorophenyl | b.p.$_{0.05}$ = 205–210° C. |
| 10 | 2-EtO-pyridin-5-yl | CH₃ | CH₃ | O | H | 2-(phenoxy)pyridin-5-yl | b.p.$_{0.2}$ = 235–240° C. |
| 11 | 2-EtO-pyridin-5-yl | CH₃ | CH₃ | O | H | 2-(4-fluorophenoxy)pyridin-5-yl | |
| 12 | 2-Cl-pyridin-5-yl | CH₃ | CH₃ | CH₂ | H | 4-phenoxyphenyl | b.p.$_{0.2}$ = 225–230° C. |
| 13 | 2-Cl-pyridin-5-yl | CH₃ | CH₃ | CH₂ | H | 4-(phenoxy)-3-fluorophenyl | b.p.$_{0.2}$ = 220° C. |
| 14 | 2-Cl-pyridin-5-yl | CH₃ | CH₃ | CH₂ | H | 2-(phenoxy)pyridin-5-yl | |

-continued $$R^1-\underset{\underset{R^3}{|}}{\overset{\overset{R^2}{|}}{Si}}-CH_2-X-\underset{\underset{R^4}{|}}{CH}-R^5$$

| Example No. | R¹ | R² | R³ | X | R⁴ | R⁵ | Physical Data |
|---|---|---|---|---|---|---|---|
| 15 | 2-Cl-pyridin-5-yl | CH₃ | CH₃ | CH₂ | H | 6-(4-fluorophenoxy)pyridin-3-yl | |
| 16 | 2-Cl-pyridin-5-yl | CH₃ | CH₃ | CH₂ | H | 3-fluoro-4-(4-fluorophenoxy)phenyl | |
| 17 | 2-Cl-pyridin-5-yl | CH₃ | CH₃ | CH₂ | CN | 3-fluoro-4-phenoxyphenyl | |
| 18 | 2-Cl-pyridin-5-yl | CH₃ | CH₃ | O | H | 4-phenoxyphenyl | b.p.$_{0.1}$ = 220–225° C. |
| 19 | 2-Cl-pyridin-5-yl | CH₃ | CH₃ | O | H | 3-fluoro-4-phenoxyphenyl | b.p.$_{0.2}$ = 225–230° C. |
| 20 | 2-Cl-pyridin-5-yl | CH₃ | CH₃ | O | H | 6-phenoxypyridin-3-yl | b.p.$_{0.05}$ = 210–220° C. |
| 21 | 2-Cl-pyridin-5-yl | CH₃ | CH₃ | O | H | 6-(4-fluorophenoxy)pyridin-3-yl | |
| 22 | 2-Cl-pyridin-5-yl | CH₃ | CH₃ | O | CH₃ | 4-phenoxyphenyl | b.p.$_{0.1}$ = 230–235° C. |
| 23 | 2-CH₃O-pyridin-5-yl | CH₃ | CH₃ | CH₂ | H | 4-phenoxyphenyl | b.p.$_{0.1}$ = 205–210° C. |

-continued $$R^1-\underset{R^3}{\underset{|}{\overset{R^2}{\overset{|}{Si}}}}-CH_2-X-\underset{R^4}{\overset{R^5}{\overset{|}{CH}}}$$

| Example No. | R¹ | R² | R³ | X | R⁴ | R⁵ | Physical Data |
|---|---|---|---|---|---|---|---|
| 24 | 2-H₃CO-pyridin-5-yl | CH₃ | CH₃ | CH₂ | H | 2-fluoro-phenoxyphenyl | b.p.₀.₀₅ = 200–205° C. |
| 25 | 2-H₃CO-pyridin-5-yl | CH₃ | CH₃ | CH₂ | H | pyridinyl-oxy-phenyl | |
| 26 | 2-H₃CO-pyridin-5-yl | CH₃ | CH₃ | CH₂ | H | pyridinyl-oxy-(4-fluorophenyl) | |
| 27 | 2-H₃CO-pyridin-5-yl | CH₃ | CH₃ | CH₂ | H | 2-fluoro-4-(4-fluorophenoxy)phenyl | |
| 28 | 2-H₃CO-pyridin-5-yl | CH₃ | CH₃ | CH₂ | CN | 2-fluoro-phenoxyphenyl | |
| 29 | 2-H₃CO-pyridin-5-yl | CH₃ | CH₃ | O | H | phenoxyphenyl | |
| 30 | 2-H₃CO-pyridin-5-yl | CH₃ | CH₃ | O | H | 2-fluoro-phenoxyphenyl | b.p.₀.₁ = 210–220° C. |
| 31 | 2-H₃CO-pyridin-5-yl | CH₃ | CH₃ | O | H | pyridinyl-oxy-phenyl | |
| 32 | 2-H₃CO-pyridin-5-yl | CH₃ | CH₃ | O | H | pyridinyl-oxy-(4-fluorophenyl) | |

-continued
$$R^1-\underset{\underset{R^3}{|}}{\overset{\overset{R^2}{|}}{Si}}-CH_2-X-\underset{\underset{R^4}{|}}{CH}-R^5$$
| Example No. | R¹ | R² | R³ | X | R⁴ | R⁵ | Physical Data |
|---|---|---|---|---|---|---|---|
| 33 | 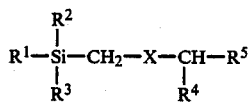 | CH₃ | CH₃ | O | CH₃ | 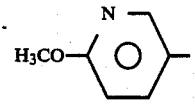 | |
| 34 | 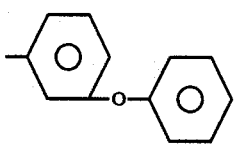 | CH₃ | CH₃ | CH₂ | H | 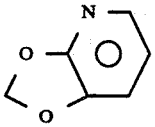 | |
| 35 | 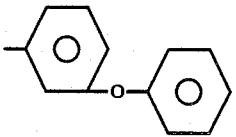 | CH₃ | CH₃ | CH₂ | H | 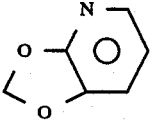 | |
| 36 | 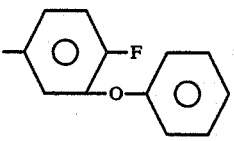 | CH₃ | CH₃ | CH₂ | H | 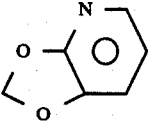 | |
| 37 | 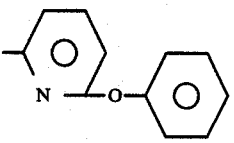 | CH₃ | CH₃ | CH₂ | H | 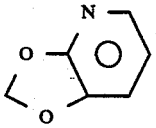 | |
| 38 | 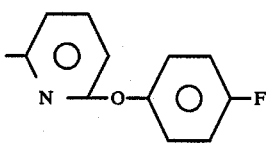 | CH₃ | CH₃ | CH₂ | H | 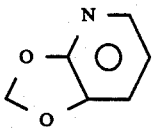 | |
| 39 | 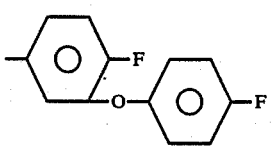 | CH₃ | CH₃ | CH₂ | CN | 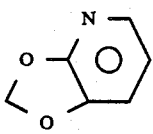 | |
| 40 | 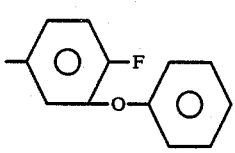 | CH₃ | CH₃ | O | H | 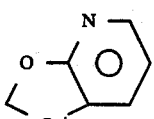 | |
| 41 | 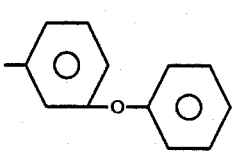 | CH₃ | CH₃ | O | H | 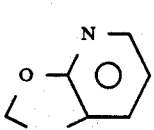 | |

-continued
$$R^1-\underset{\underset{R^3}{|}}{\overset{\overset{R^2}{|}}{Si}}-CH_2-X-\underset{\underset{R^4}{|}}{CH}-R^5$$
| Example No. | R¹ | R² | R³ | X | R⁴ | R⁵ | Physical Data |
|---|---|---|---|---|---|---|---|
| 42 | 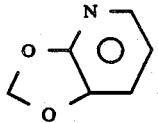 | CH₃ | CH₃ | O | H | 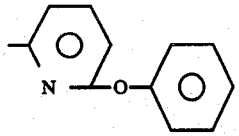 | |
| 43 | 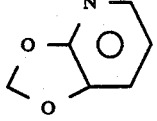 | CH₃ | CH₃ | O | H | 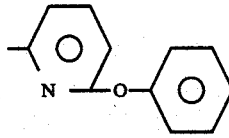 | |
| 44 | 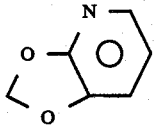 | CH₃ | CH₃ | O | CH₃ | 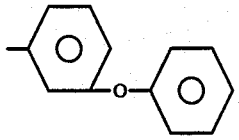 | |
| 45 | 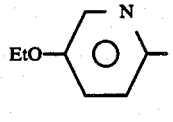 | CH₃ | CH₃ | CH₂ | H | 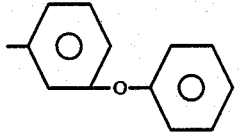 | b.p.$_{0.2}$ = 235° C. |
| 46 | 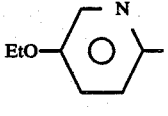 | CH₃ | CH₃ | CH₂ | H | 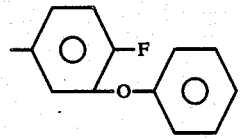 | b.p.$_{0.15}$ = 225–230° C. |
| 47 | 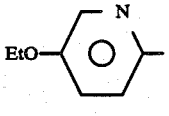 | CH₃ | CH₃ | CH₂ | H | 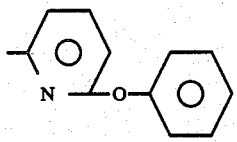 | |
| 48 | 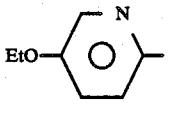 | CH₃ | CH₃ | CH₂ | H | 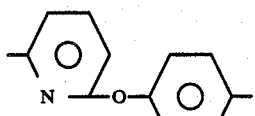 | |
| 49 | 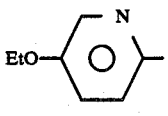 | CH₃ | CH₃ | CH₂ | H | 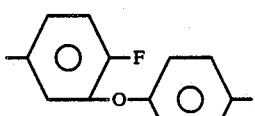 | |
| 50 | 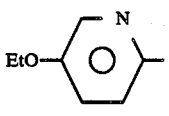 | CH₃ | CH₃ | CH₂ | CN | 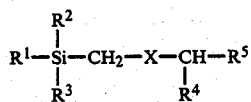 | pale yellow oil |

-continued $$R^1-\underset{\underset{R^3}{|}}{\overset{\overset{R^2}{|}}{Si}}-CH_2-X-\underset{\underset{R^4}{|}}{CH}-R^5$$

| Example No. | R¹ | R² | R³ | X | R⁴ | R⁵ | Physical Data |
|---|---|---|---|---|---|---|---|
| 51 | 5-ethoxypyridin-2-yl | CH₃ | CH₃ | O | H | phenoxyphenyl | b.p.$_{0.2}$ = 230–240° C. |
| 52 | 5-ethoxypyridin-2-yl | CH₃ | CH₃ | O | H | 2-fluoro-phenoxyphenyl | b.p.$_{0.15}$ = 230–235° C. |
| 53 | 5-ethoxypyridin-2-yl | CH₃ | CH₃ | O | H | (pyridin-2-yl)oxyphenyl | b.p.$_{0.2}$ = 235–240° C. |
| 54 | 5-ethoxypyridin-2-yl | CH₃ | CH₃ | O | H | (pyridin-2-yl)oxy-4-fluorophenyl | |
| 55 | 5-ethoxypyridin-2-yl | CH₃ | CH₃ | O | CH₃ | phenoxyphenyl | |
| 56 | 5-chloropyridin-2-yl | CH₃ | CH₃ | CH₂ | H | phenoxyphenyl | b.p.$_{0.02}$ = 190–200° C. |
| 57 | 5-chloropyridin-2-yl | CH₃ | CH₃ | CH₂ | H | 2-fluoro-phenoxyphenyl | b.p.$_{0.1}$ = 205–215° C. |
| 58 | 5-chloropyridin-2-yl | CH₃ | CH₃ | CH₂ | H | (pyridin-2-yl)oxyphenyl | |
| 59 | 5-chloropyridin-2-yl | CH₃ | CH₃ | CH₂ | H | (pyridin-2-yl)oxy-4-fluorophenyl | |

-continued

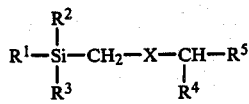

| Example No. | R¹ | R² | R³ | X | R⁴ | R⁵ | Physical Data |
|---|---|---|---|---|---|---|---|
| 60 | 5-Cl-pyridin-2-yl | CH₃ | CH₃ | CH₂ | H | 2-fluoro-4-(4-fluorophenoxy)phenyl | |
| 61 | 5-Cl-pyridin-2-yl | CH₃ | CH₃ | CH₂ | CN | 2-fluoro-4-phenoxyphenyl | |
| 62 | 5-Cl-pyridin-2-yl | CH₃ | CH₃ | O | H | 4-phenoxyphenyl | b.p.$_{0.2}$ = 215–220° C. |
| 63 | 5-Cl-pyridin-2-yl | CH₃ | CH₃ | O | H | 2-fluoro-4-phenoxyphenyl | b.p.$_{0.2}$ = 210–215° C. |
| 64 | 5-Cl-pyridin-2-yl | CH₃ | CH₃ | O | H | 5-phenoxy-pyridin-2-yl | |
| 65 | 5-Cl-pyridin-2-yl | CH₃ | CH₃ | O | H | 5-(4-fluorophenoxy)-pyridin-2-yl | |
| 66 | 5-Cl-pyridin-2-yl | CH₃ | CH₃ | O | CH₃ | 4-phenoxyphenyl | |
| 67 | 5-H₃CO-pyridin-2-yl | CH₃ | CH₃ | CH₂ | H | 4-phenoxyphenyl | |
| 68 | 5-H₃CO-pyridin-2-yl | CH₃ | CH₃ | CH₂ | H | 2-fluoro-4-phenoxyphenyl | b.p.$_{0.1}$ = 210–220° C. |

-continued

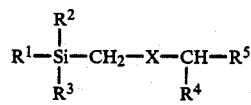

| Example No. | R¹ | R² | R³ | X | R⁴ | R⁵ | Physical Data |
|---|---|---|---|---|---|---|---|
| 69 | H₃CO-pyridine | CH₃ | CH₃ | CH₂ | H | pyridine-O-phenyl | |
| 70 | H₃CO-pyridine | CH₃ | CH₃ | CH₂ | H | pyridine-O-phenyl-F | |
| 71 | H₃CO-pyridine | CH₃ | CH₃ | CH₂ | H | phenyl(F)-O-phenyl-F | |
| 72 | H₃CO-pyridine | CH₃ | CH₃ | CH₂ | CN | phenyl(F)-O-phenyl | |
| 73 | H₃CO-pyridine | CH₃ | CH₃ | O | H | phenyl-O-phenyl | |
| 74 | H₃CO-pyridine | CH₃ | CH₃ | O | H | phenyl(F)-O-phenyl | b.p.$_{0.05}$ = 210–215° C. |
| 75 | H₃CO-pyridine | CH₃ | CH₃ | O | H | pyridine-O-phenyl | |
| 76 | H₃CO-pyridine | CH₃ | CH₃ | O | H | pyridine-O-phenyl-F | |
| 77 | H₃CO-pyridine | CH₃ | CH₃ | O | CH₃ | phenyl-O-phenyl | |

-continued

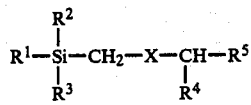

| Example No. | R¹ | R² | R³ | X | R⁴ | R⁵ | Physical Data |
|---|---|---|---|---|---|---|---|
| 78 | (1,3-dioxolano-pyridinyl) | CH₃ | CH₃ | CH₂ | H | phenoxyphenyl | |
| 79 | (1,3-dioxolano-pyridinyl) | CH₃ | CH₃ | CH₂ | H | (2-fluoro-phenoxy)phenyl | |
| 80 | (1,3-dioxolano-pyridinyl) | CH₃ | CH₃ | CH₂ | H | (pyridinyloxy)phenyl | |
| 81 | (1,3-dioxolano-pyridinyl) | CH₃ | CH₃ | CH₂ | H | (4-fluorophenoxy)pyridinyl | |
| 82 | (1,3-dioxolano-pyridinyl) | CH₃ | CH₃ | CH₂ | H | (2-fluoro-4-fluorophenoxy)phenyl | |
| 83 | (1,3-dioxolano-pyridinyl) | CH₃ | CH₃ | CH₂ | CN | (2-fluorophenoxy)phenyl | |
| 84 | (1,3-dioxolano-pyridinyl) | CH₃ | CH₃ | O | H | phenoxyphenyl | |
| 85 | (1,3-dioxolano-pyridinyl) | CH₃ | CH₃ | O | H | (2-fluorophenoxy)phenyl | |
| 86 | (1,3-dioxolano-pyridinyl) | CH₃ | CH₃ | O | H | (phenoxy)pyridinyl | |

-continued

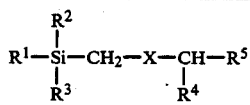

| Example No. | R¹ | R² | R³ | X | R⁴ | R⁵ | Physical Data |
|---|---|---|---|---|---|---|---|
| 87 | dioxolo-pyridyl | CH₃ | CH₃ | O | H | pyridyl-O-phenyl-F | |
| 88 | dioxolo-pyridyl | CH₃ | CH₃ | O | CH₃ | phenyl-O-phenyl | |
| 89 | dioxolo-pyridyl | CH₃ | CH₃ | CH₂ | H | phenyl-O-phenyl | |
| 90 | dioxolo-pyridyl | CH₃ | CH₃ | CH₂ | H | phenyl(F)-O-phenyl | |
| 91 | dioxolo-pyridyl | CH₃ | CH₃ | CH₂ | H | pyridyl-O-phenyl | |
| 92 | dioxolo-pyridyl | CH₃ | CH₃ | CH₂ | H | pyridyl-O-phenyl-F | |
| 93 | dioxolo-pyridyl | CH₃ | CH₃ | CH₂ | H | phenyl(F)-O-phenyl-F | |
| 94 | dioxolo-pyridyl | CH₃ | CH₃ | CH₂ | CN | phenyl(F)-O-phenyl | |
| 95 | dioxolo-pyridyl | CH₃ | CH₃ | O | H | phenyl-O-phenyl | |

-continued

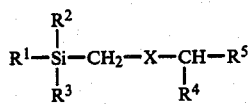

| Example No. | R¹ | R² | R³ | X | R⁴ | R⁵ | Physical Data |
|---|---|---|---|---|---|---|---|
| 96 | [benzodioxole-pyridine] | CH₃ | CH₃ | O | H | [phenyl-O-phenyl with F] | |
| 97 | [benzodioxole-pyridine] | CH₃ | CH₃ | O | H | [pyridyl-O-phenyl] | |
| 98 | [benzodioxole-pyridine] | CH₃ | CH₃ | O | H | [pyridyl-O-phenyl-F] | |
| 99 | [benzodioxole-pyridine] | CH₃ | CH₃ | O | CH₃ | [phenyl-O-phenyl] | |
| 100 | [EtO-pyrimidine] | CH₃ | CH₃ | CH₂ | H | [phenyl-O-phenyl] | b.p.$_{0.3}$ = 250° C. |
| 101 | [EtO-pyrimidine] | CH₃ | CH₃ | CH₂ | H | [phenyl-O-phenyl-F] | b.p.$_{0.15}$ = 235–240° C. |
| 102 | [EtO-pyrimidine] | CH₃ | CH₃ | CH₂ | H | [pyridyl-O-phenyl] | pale yellow oil |
| 103 | [EtO-pyrimidine] | CH₃ | CH₃ | CH₂ | H | [pyridyl-O-phenyl-F] | |
| 104 | [EtO-pyrimidine] | CH₃ | CH₃ | CH₂ | H | [phenyl-F-O-phenyl-F] | |

-continued

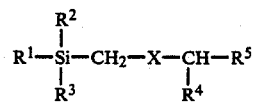

| Example No. | R¹ | R² | R³ | X | R⁴ | R⁵ | Physical Data |
|---|---|---|---|---|---|---|---|
| 105 | EtO-(pyrimidine)- | CH₃ | CH₃ | CH₂ | CN | -(C₆H₄)-O-(F-C₆H₄) | |
| 106 | EtO-(pyrimidine)- | CH₃ | CH₃ | O | H | -(C₆H₄)-O-(C₆H₅) | b.p.$_{0.05}$ = 220° C. |
| 107 | EtO-(pyrimidine)- | CH₃ | CH₃ | O | H | -(C₆H₄)-O-(F-C₆H₄) | b.p.$_{0.05}$ = 215–220° C. |
| 108 | EtO-(pyrimidine)- | CH₃ | CH₃ | O | H | -(pyridyl)-O-(C₆H₅) | |
| 109 | EtO-(pyrimidine)- | CH₃ | CH₃ | O | H | -(pyridyl)-O-(F-C₆H₄) | |
| 110 | EtO-(pyrimidine)- | CH₃ | CH₃ | O | CH₃ | -(C₆H₄)-O-(C₆H₅) | |
| 111 | Cl-(pyrimidine)- | CH₃ | CH₃ | CH₂ | H | -(C₆H₄)-O-(C₆H₅) | b.p.$_{0.1}$ = 235–240° C. |
| 112 | Cl-(pyrimidine)- | CH₃ | CH₃ | CH₂ | H | -(C₆H₄)-O-(F-C₆H₄) | b.p.$_{0.05}$ = 230–235° C. |
| 113 | Cl-(pyrimidine)- | CH₃ | CH₃ | CH₂ | H | -(pyridyl)-O-(C₆H₅) | |

-continued $$R^1-\underset{\underset{R^3}{|}}{\overset{\overset{R^2}{|}}{Si}}-CH_2-X-\underset{\underset{R^4}{|}}{CH}-R^5$$

| Example No. | R¹ | R² | R³ | X | R⁴ | R⁵ | Physical Data |
|---|---|---|---|---|---|---|---|
| 114 | 2-Cl-pyrimidin-5-yl | CH₃ | CH₃ | CH₂ | H | 6-(4-fluorophenoxy)pyridin-3-yl | |
| 115 | 2-Cl-pyrimidin-5-yl | CH₃ | CH₃ | CH₂ | H | 3-fluoro-4-(4-fluorophenoxy)phenyl | |
| 116 | 2-Cl-pyrimidin-5-yl | CH₃ | CH₃ | CH₂ | CN | 3-fluoro-4-phenoxyphenyl | |
| 117 | 2-Cl-pyrimidin-5-yl | CH₃ | CH₃ | O | H | 4-phenoxyphenyl | b.p.₀.₀₅ = 235–240° C. |
| 118 | 2-Cl-pyrimidin-5-yl | CH₃ | CH₃ | O | H | 3-fluoro-4-phenoxyphenyl | b.p.₀.₁ = 240° C. |
| 119 | 2-Cl-pyrimidin-5-yl | CH₃ | CH₃ | O | H | 6-phenoxypyridin-3-yl | |
| 120 | 2-Cl-pyrimidin-5-yl | CH₃ | CH₃ | O | H | 6-(4-fluorophenoxy)pyridin-3-yl | |
| 121 | 2-Cl-pyrimidin-5-yl | CH₃ | CH₃ | O | CH₃ | 4-phenoxyphenyl | |
| 122 | 2-CH₃O-pyrimidin-5-yl | CH₃ | CH₃ | CH₂ | H | 4-phenoxyphenyl | b.p.₀.₀₅ = 235–245° C. |

-continued $$R^1-\underset{\underset{R^3}{|}}{\overset{\overset{R^2}{|}}{Si}}-CH_2-X-\underset{\underset{R^4}{|}}{CH}-R^5$$

| Example No. | R¹ | R² | R³ | X | R⁴ | R⁵ | Physical Data |
|---|---|---|---|---|---|---|---|
| 123 | 2-methoxypyrimidin-5-yl | CH₃ | CH₃ | CH₂ | H | 3-fluoro-4-phenoxyphenyl | b.p.$_{0.1}$ = 240° C. |
| 124 | 2-methoxypyrimidin-5-yl | CH₃ | CH₃ | CH₂ | H | 6-phenoxypyridin-3-yl | |
| 125 | 2-methoxypyrimidin-5-yl | CH₃ | CH₃ | CH₂ | H | 6-(4-fluorophenoxy)pyridin-3-yl | |
| 126 | 2-methoxypyrimidin-5-yl | CH₃ | CH₃ | CH₂ | H | 3-fluoro-4-(4-fluorophenoxy)phenyl | |
| 127 | 2-methoxypyrimidin-5-yl | CH₃ | CH₃ | CH₂ | CN | 3-fluoro-4-phenoxyphenyl | |
| 128 | 2-methoxypyrimidin-5-yl | CH₃ | CH₃ | O | H | 4-phenoxyphenyl | pale yellow oil |
| 129 | 2-methoxypyrimidin-5-yl | CH₃ | CH₃ | O | H | 3-fluoro-4-phenoxyphenyl | b.p.$_{0.02}$ = 230–235° C. |
| 130 | 2-methoxypyrimidin-5-yl | CH₃ | CH₃ | O | H | 6-phenoxypyridin-3-yl | |
| 131 | 2-methoxypyrimidin-5-yl | CH₃ | CH₃ | O | H | 6-(4-fluorophenoxy)pyridin-3-yl | |

-continued $$R^1-\underset{R^3}{\overset{R^2}{Si}}-CH_2-X-\underset{R^4}{CH}-R^5$$

| Example No. | R¹ | R² | R³ | X | R⁴ | R⁵ | Physical Data |
|---|---|---|---|---|---|---|---|
| 132 | 2-methoxy-pyrimidin-5-yl (H₃CO-pyrimidinyl) | CH₃ | CH₃ | O | CH₃ | 4-phenoxyphenyl | |

$$R^1-\underset{R^3}{\overset{R^2}{Si}}-CH_2-X-\underset{R^4}{CH}-R^5$$

| Example No. | R¹ | R² | R³ | X | R⁴ | R⁵ | Physical Data |
|---|---|---|---|---|---|---|---|
| 133 | 2-ethyl-pyrimidin-5-yl | CH₃ | CH₃ | CH₂ | H | 4-phenoxyphenyl | |
| 134 | 2-ethyl-pyrimidin-5-yl | CH₃ | CH₃ | CH₂ | H | 3-fluoro-4-phenoxyphenyl | b.p.$_{0.05}$ = 235–240° C. |
| 135 | 2-ethyl-pyrimidin-5-yl | CH₃ | CH₃ | CH₂ | H | 6-phenoxy-pyridin-3-yl | |
| 136 | 2-ethyl-pyrimidin-5-yl | CH₃ | CH₃ | CH₂ | H | 6-(4-fluorophenoxy)-pyridin-3-yl | |
| 137 | 2-ethyl-pyrimidin-5-yl | CH₃ | CH₃ | CH₂ | H | 3-fluoro-4-(4-fluorophenoxy)phenyl | |
| 138 | 2-ethyl-pyrimidin-5-yl | CH₃ | CH₃ | CH₂ | CN | 3-fluoro-4-phenoxyphenyl | |
| 139 | 2-ethyl-pyrimidin-5-yl | CH₃ | CH₃ | O | H | 4-phenoxyphenyl | |

-continued $$R^1-\underset{\underset{R^3}{|}}{\overset{\overset{R^2}{|}}{Si}}-CH_2-X-\underset{\underset{R^4}{|}}{CH}-R^5$$

| Example No. | R¹ | R² | R³ | X | R⁴ | R⁵ | Physical Data |
|---|---|---|---|---|---|---|---|
| 140 | 2-Et-pyrimidin-5-yl | CH₃ | CH₃ | O | H | 3-(phenoxy)-4-fluorophenyl | b.p.·0.02 = 240° C. |
| 141 | 2-Et-pyrimidin-5-yl | CH₃ | CH₃ | O | H | 6-(phenoxy)pyridin-3-yl | |
| 142 | 2-Et-pyrimidin-5-yl | CH₃ | CH₃ | O | H | 6-(4-fluorophenoxy)pyridin-3-yl | |
| 143 | 2-Et-pyrimidin-5-yl | CH₃ | CH₃ | O | CH₃ | 3-(phenoxy)phenyl | |
| 144 | 2-C₃H₇-pyrimidin-5-yl | CH₃ | CH₃ | CH₂ | H | 3-(phenoxy)phenyl | b.p.·0.02 = 235–245° C. |
| 145 | 2-C₃H₇-pyrimidin-5-yl | CH₃ | CH₃ | CH₂ | H | 3-(phenoxy)-4-fluorophenyl | |
| 146 | 2-C₃H₇-pyrimidin-5-yl | CH₃ | CH₃ | CH₂ | H | 6-(phenoxy)pyridin-3-yl | |
| 147 | 2-C₃H₇-pyrimidin-5-yl | CH₃ | CH₃ | CH₂ | H | 6-(4-fluorophenoxy)pyridin-3-yl | |
| 148 | 2-C₃H₇-pyrimidin-5-yl | CH₃ | CH₃ | CH₂ | H | 3-(4-fluorophenoxy)-4-fluorophenyl | |

-continued $$R^1-\underset{\underset{R^3}{|}}{\overset{\overset{R^2}{|}}{Si}}-CH_2-X-\underset{R^4}{\overset{|}{CH}}-R^5$$

| Example No. | R¹ | R² | R³ | X | R⁴ | R⁵ | Physical Data |
|---|---|---|---|---|---|---|---|
| 149 | C₃H₇-pyrimidinyl | CH₃ | CH₃ | CH₂ | CN | fluorophenoxyphenyl | |
| 150 | C₃H₇-pyrimidinyl | CH₃ | CH₃ | O | H | phenoxyphenyl | |
| 151 | C₃H₇-pyrimidinyl | CH₃ | CH₃ | O | H | fluorophenoxyphenyl | b.p.$_{0.04}$ = 240–250° C. |
| 152 | C₃H₇-pyrimidinyl | CH₃ | CH₃ | O | H | phenoxypyridinyl | |
| 153 | C₃H₇-pyrimidinyl | CH₃ | CH₃ | O | H | (4-fluorophenoxy)pyridinyl | |
| 154 | C₃H₇-pyrimidinyl | CH₃ | CH₃ | O | CH₃ | phenoxyphenyl | |
| 155 | EtO-pyrimidinyl | CH₃ | CH₃ | CH₂ | H | phenoxyphenyl | |
| 156 | EtO-pyrimidinyl | CH₃ | CH₃ | CH₂ | H | fluorophenoxyphenyl | b.p.$_{0.05}$ = 210–220° C. |
| 157 | EtO-pyrimidinyl | CH₃ | CH₃ | CH₂ | H | phenoxypyridinyl | |

-continued

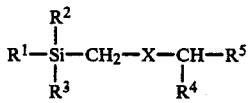

| Example No. | R¹ | R² | R³ | X | R⁴ | R⁵ | Physical Data |
|---|---|---|---|---|---|---|---|
| 158 | EtO-pyrimidine | CH₃ | CH₃ | CH₂ | H | pyridine-O-C₆H₄-F | |
| 159 | EtO-pyrimidine | CH₃ | CH₃ | CH₂ | H | C₆H₃F-O-C₆H₄-F | |
| 160 | EtO-pyrimidine | CH₃ | CH₃ | CH₂ | CN | C₆H₃F-O-C₆H₅ | |
| 161 | EtO-pyrimidine | CH₃ | CH₃ | O | H | C₆H₄-O-C₆H₅ | b.p.$_{0.02}$ = 220–225° C. |
| 162 | EtO-pyrimidine | CH₃ | CH₃ | O | H | C₆H₃F-O-C₆H₅ | b.p.$_{0.1}$ = 230–235° C. |
| 163 | EtO-pyrimidine | CH₃ | CH₃ | O | H | pyridine-O-C₆H₅ | |
| 164 | EtO-pyrimidine | CH₃ | CH₃ | O | H | pyridine-O-C₆H₄-F | |
| 165 | EtO-pyrimidine | CH₃ | CH₃ | O | CH₃ | C₆H₄-O-C₆H₅ | |
| 166 | Cl-pyrimidine | CH₃ | CH₃ | CH₂ | H | C₆H₄-O-C₆H₅ | |

-continued

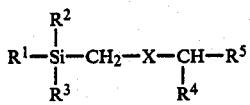

| Example No. | R¹ | R² | R³ | X | R⁴ | R⁵ | Physical Data |
|---|---|---|---|---|---|---|---|
| 167 | Cl-pyrimidine | CH₃ | CH₃ | CH₂ | H | phenyl-O-phenyl with F | |
| 168 | Cl-pyrimidine | CH₃ | CH₃ | CH₂ | H | pyridyl-O-phenyl | |
| 169 | Cl-pyrimidine | CH₃ | CH₃ | CH₂ | H | pyridyl-O-phenyl-F | |
| 170 | Cl-pyrimidine | CH₃ | CH₃ | CH₂ | H | phenyl(F)-O-phenyl-F | |
| 171 | Cl-pyrimidine | CH₃ | CH₃ | CH₂ | CN | phenyl(F)-O-phenyl | |
| 172 | Cl-pyrimidine | CH₃ | CH₃ | O | H | phenyl-O-phenyl | |
| 173 | Cl-pyrimidine | CH₃ | CH₃ | O | H | phenyl(F)-O-phenyl | |
| 174 | Cl-pyrimidine | CH₃ | CH₃ | O | H | pyridyl-O-phenyl | |
| 175 | Cl-pyrimidine | CH₃ | CH₃ | O | H | pyridyl-O-phenyl-F | |

-continued
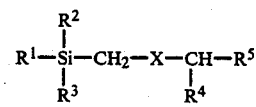
| Example No. | R¹ | R² | R³ | X | R⁴ | R⁵ | Physical Data |
|---|---|---|---|---|---|---|---|
| 176 | 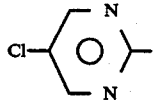 | CH₃ | CH₃ | O | CH₃ | 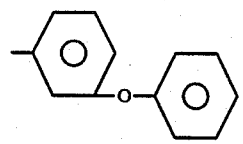 | |
| 177 | 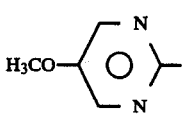 | CH₃ | CH₃ | CH₂ | H | 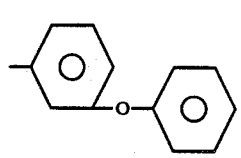 | |
| 178 | 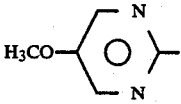 | CH₃ | CH₃ | CH₂ | H | 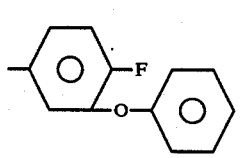 | |
| 179 | 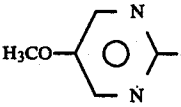 | CH₃ | CH₃ | CH₂ | H | 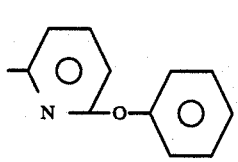 | |
| 180 | 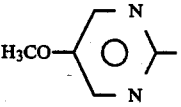 | CH₃ | CH₃ | CH₂ | H | 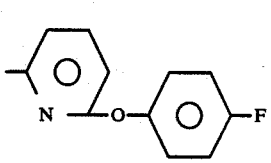 | |
| 181 | 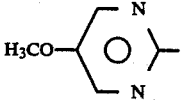 | CH₃ | CH₃ | CH₂ | H | 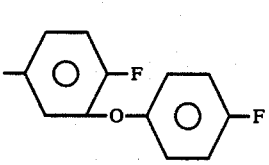 | |
| 182 | 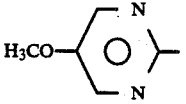 | CH₃ | CH₃ | CH₂ | CN | 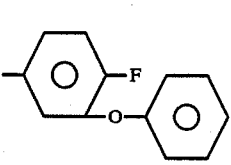 | |
| 183 | 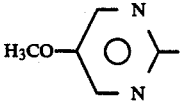 | CH₃ | CH₃ | O | H | 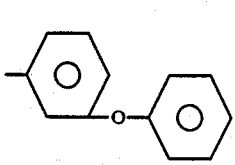 | |
| 184 | 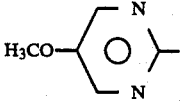 | CH₃ | CH₃ | O | H | 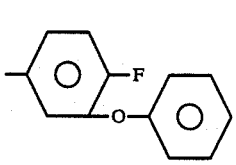 | |

4,775,664

-continued

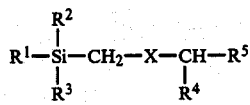

| Example No. | R¹ | R² | R³ | X | R⁴ | R⁵ | Physical Data |
|---|---|---|---|---|---|---|---|
| 185 | H₃CO—[pyrimidine] | CH₃ | CH₃ | O | H | [pyridine]—O—[phenyl] | |
| 186 | H₃CO—[pyrimidine] | CH₃ | CH₃ | O | H | [pyridine]—O—[phenyl]-F | |
| 187 | H₃CO—[pyrimidine] | CH₃ | CH₃ | O | CH₃ | [phenyl]—O—[phenyl] | |
| 188 | CH₃—[pyrimidine] | CH₃ | CH₃ | CH₂ | H | [phenyl]—O—[phenyl] | |
| 189 | CH₃—[pyrimidine] | CH₃ | CH₃ | CH₂ | H | [phenyl]-F—O—[phenyl] | |
| 190 | CH₃—[pyrimidine] | CH₃ | CH₃ | CH₂ | H | [pyridine]—O—[phenyl] | |
| 191 | CH₃—[pyrimidine] | CH₃ | CH₃ | CH₂ | H | [pyridine]—O—[phenyl]-F | |
| 192 | CH₃—[pyrimidine] | CH₃ | CH₃ | CH₂ | H | [phenyl]-F—O—[phenyl]-F | |
| 193 | CH₃—[pyrimidine] | CH₃ | CH₃ | CH₂ | CN | [phenyl]-F—O—[phenyl] | |

-continued

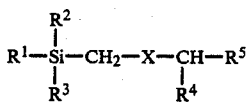

| Example No. | R¹ | R² | R³ | X | R⁴ | R⁵ | Physical Data |
|---|---|---|---|---|---|---|---|
| 194 | CH₃-[4-methylpyrimidin-2-yl] | CH₃ | CH₃ | O | H | -C₆H₄-O-C₆H₅ | |
| 195 | CH₃-[4-methylpyrimidin-2-yl] | CH₃ | CH₃ | O | H | -C₆H₃(F)-O-C₆H₅ | |
| 196 | CH₃-[4-methylpyrimidin-2-yl] | CH₃ | CH₃ | O | H | -[pyridin-2-yl]-O-C₆H₅ | |
| 197 | CH₃-[4-methylpyrimidin-2-yl] | CH₃ | CH₃ | O | H | -[pyridin-2-yl]-O-C₆H₄-F | |
| 198 | CH₃-[4-methylpyrimidin-2-yl] | CH₃ | CH₃ | O | CH₃ | -C₆H₄-O-C₆H₅ | |
| 199 | Et-[pyrimidin-2-yl] | CH₃ | CH₃ | CH₂ | H | -C₆H₄-O-C₆H₅ | |
| 200 | Et-[pyrimidin-2-yl] | CH₃ | CH₃ | CH₂ | H | -C₆H₃(F)-O-C₆H₅ | |
| 201 | Et-[pyrimidin-2-yl] | CH₃ | CH₃ | CH₂ | H | -[pyridin-2-yl]-O-C₆H₅ | |
| 202 | Et-[pyrimidin-2-yl] | CH₃ | CH₃ | CH₂ | H | -[pyridin-2-yl]-O-C₆H₄-F | |

-continued
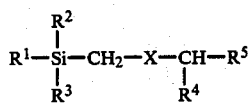
| Example No. | R¹ | R² | R³ | X | R⁴ | R⁵ | Physical Data |
|---|---|---|---|---|---|---|---|
| 203 | 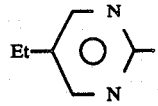 | CH₃ | CH₃ | CH₂ | H | 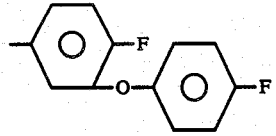 | |
| 204 | 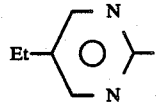 | CH₃ | CH₃ | CH₂ | CN | 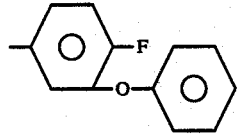 | |
| 205 | 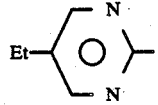 | CH₃ | CH₃ | O | H | 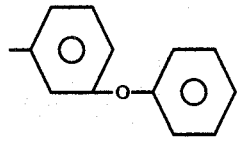 | |
| 206 | 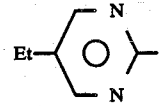 | CH₃ | CH₃ | O | H | 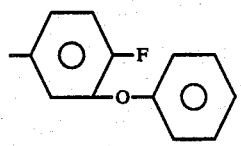 | |
| 207 | 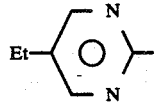 | CH₃ | CH₃ | O | H | 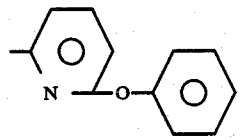 | |
| 208 | 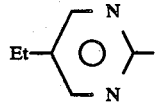 | CH₃ | CH₃ | O | H | 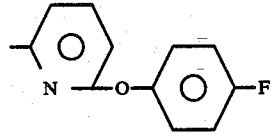 | |
| 209 | 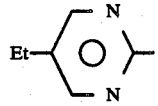 | CH₃ | CH₃ | O | CH₃ | 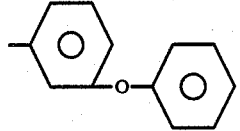 | |
| 210 | 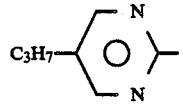 | CH₃ | CH₃ | CH₂ | H | 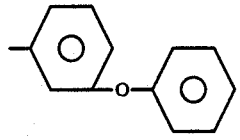 | |
| 211 | 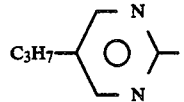 | CH₃ | CH₃ | CH₂ | H | 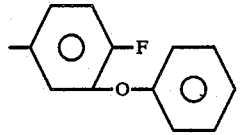 | |

-continued
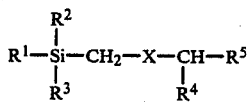
| Example No. | R¹ | R² | R³ | X | R⁴ | R⁵ | Physical Data |
|---|---|---|---|---|---|---|---|
| 212 | 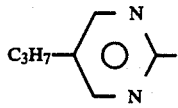 | CH₃ | CH₃ | CH₂ | H | 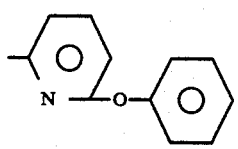 | |
| 213 | 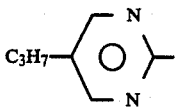 | CH₃ | CH₃ | CH₂ | H | 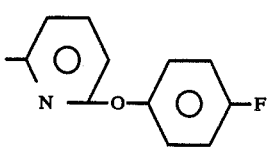 | |
| 214 | 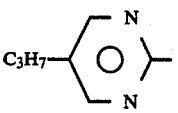 | CH₃ | CH₃ | CH₂ | H | 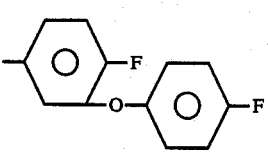 | |
| 215 | 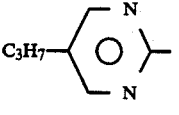 | CH₃ | CH₃ | CH₂ | CN | 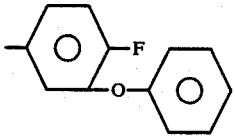 | |
| 216 | 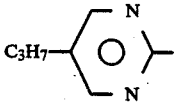 | CH₃ | CH₃ | O | H | 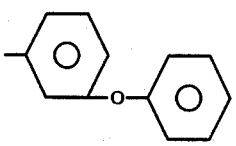 | |
| 217 | 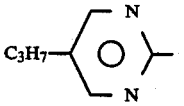 | CH₃ | CH₃ | O | H | 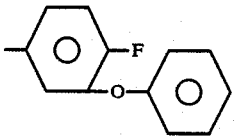 | |
| 218 | 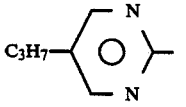 | CH₃ | CH₃ | O | H | 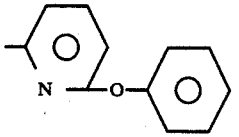 | |
| 219 | 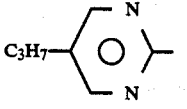 | CH₃ | CH₃ | O | H | 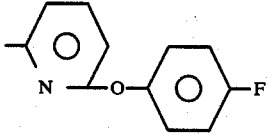 | |
| 220 | 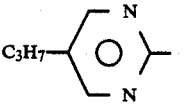 | CH₃ | CH₃ | O | CH₃ | 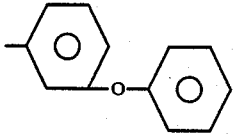 | |

-continued

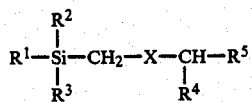

| Example No. | R¹ | R² | R³ | X | R⁴ | R⁵ | Physical Data |
|---|---|---|---|---|---|---|---|
| 221 | (dioxolane-pyrazine) | CH₃ | CH₃ | CH₂ | H | (phenyl-O-phenyl) | |
| 222 | (dioxolane-pyrazine) | CH₃ | CH₃ | CH₂ | H | (F-phenyl-O-phenyl) | |
| 223 | (dioxolane-pyrazine) | CH₃ | CH₃ | CH₂ | H | (pyridyl-O-phenyl) | |
| 224 | (dioxolane-pyrazine) | CH₃ | CH₃ | CH₂ | H | (pyridyl-O-phenyl-F) | |
| 225 | (dioxolane-pyrazine) | CH₃ | CH₃ | CH₂ | H | (F-phenyl-O-phenyl-F) | |
| 226 | (dioxolane-pyrazine) | CH₃ | CH₃ | CH₂ | CN | (F-phenyl-O-phenyl) | |
| 227 | (dioxolane-pyrazine) | CH₃ | CH₃ | O | H | (phenyl-O-phenyl) | |
| 228 | (dioxolane-pyrazine) | CH₃ | CH₃ | O | H | (F-phenyl-O-phenyl) | |
| 229 | (dioxolane-pyrazine) | CH₃ | CH₃ | O | H | (pyridyl-O-phenyl) | |

-continued

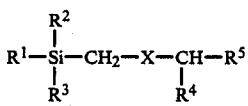

| Example No. | R¹ | R² | R³ | X | R⁴ | R⁵ | Physical Data |
|---|---|---|---|---|---|---|---|
| 230 | [1,3-dioxolo-pyrimidine] | CH₃ | CH₃ | O | H | [pyridyl-O-phenyl-F] | |
| 231 | [1,3-dioxolo-pyrimidine] | CH₃ | CH₃ | O | CH₃ | [phenyl-O-phenyl] | |
| 232 | [F₂CHO-pyridyl] | CH₃ | CH₃ | CH₂ | H | [phenyl-O-phenyl] | |
| 233 | [F₂CHO-pyridyl] | CH₃ | CH₃ | CH₂ | H | [phenyl-F-O-phenyl] | |
| 234 | [F₂CHO-pyridyl] | CH₃ | CH₃ | CH₂ | H | [pyridyl-O-phenyl] | |
| 235 | [F₂CHO-pyridyl] | CH₃ | CH₃ | CH₂ | H | [pyridyl-O-phenyl-F] | |
| 236 | [F₂CHO-pyridyl] | CH₃ | CH₃ | CH₂ | H | [phenyl-F-O-phenyl-F] | |
| 237 | [F₂CHO-pyridyl] | CH₃ | CH₃ | CH₂ | CN | [phenyl-F-O-phenyl] | |
| 238 | [F₂CHO-pyridyl] | CH₃ | CH₃ | O | H | [phenyl-O-phenyl] | |

-continued $$R^1-\underset{\underset{R^3}{|}}{\overset{\overset{R^2}{|}}{Si}}-CH_2-X-\underset{\underset{R^4}{|}}{CH}-R^5$$

| Example No. | R¹ | R² | R³ | X | R⁴ | R⁵ | Physical Data |
|---|---|---|---|---|---|---|---|
| 239 | F₂CHO-[pyridine]- | CH₃ | CH₃ | O | H | -[phenyl]-O-[phenyl] with F | |
| 240 | F₂CHO-[pyridine]- | CH₃ | CH₃ | O | H | -[pyridine]-O-[phenyl] | |
| 241 | F₂CHO-[pyridine]- | CH₃ | CH₃ | O | H | -[pyridine]-O-[phenyl]-F | |
| 242 | F₂CHO-[pyridine]- | CH₃ | CH₃ | O | CH₃ | -[phenyl]-O-[phenyl] | |
| 243 | F₂CHO-[pyrimidine]- | CH₃ | CH₃ | CH₂ | H | -[phenyl]-O-[phenyl] | |
| 244 | F₂CHO-[pyrimidine]- | CH₃ | CH₃ | CH₂ | H | -[phenyl]-O-[phenyl] with F | |
| 245 | F₂CHO-[pyrimidine]- | CH₃ | CH₃ | CH₂ | H | -[pyridine]-O-[phenyl] | |
| 246 | F₂CHO-[pyrimidine]- | CH₃ | CH₃ | CH₂ | H | -[pyridine]-O-[phenyl]-F | |
| 247 | F₂CHO-[pyrimidine]- | CH₃ | CH₃ | CH₂ | H | -[phenyl]-F-O-[phenyl]-F | |

-continued $$R^1-\underset{\underset{R^3}{|}}{\overset{\overset{R^2}{|}}{Si}}-CH_2-X-\underset{\underset{R^4}{|}}{CH}-R^5$$

| Example No. | R¹ | R² | R³ | X | R⁴ | R⁵ | Physical Data |
|---|---|---|---|---|---|---|---|
| 248 | F₂CHO—[pyrimidine] | CH₃ | CH₃ | CH₂ | CN | [phenyl-O-phenyl, F] | |
| 249 | F₂CHO—[pyrimidine] | CH₃ | CH₃ | O | H | [phenyl-O-phenyl] | |
| 250 | F₂CHO—[pyrimidine] | CH₃ | CH₃ | O | H | [phenyl-O-phenyl, F] | |
| 251 | F₂CHO—[pyrimidine] | CH₃ | CH₃ | O | H | [pyridyl-O-phenyl] | |
| 252 | F₂CHO—[pyrimidine] | CH₃ | CH₃ | O | H | [pyridyl-O-phenyl-F] | |
| 253 | F₂CHO—[pyrimidine] | CH₃ | CH₃ | O | CH₃ | [phenyl-O-phenyl] | |
| 254 | F₂CHO—[pyridyl] | H₃ | CH₃ | CH₂ | H | [phenyl-O-phenyl] | |
| 255 | F₂CHO—[pyridyl] | CH₃ | CH₃ | CH₂ | H | [phenyl-O-phenyl, F] | |
| 256 | F₂CHO—[pyridyl] | CH₃ | CH₃ | CH₂ | H | [pyridyl-O-phenyl] | |

-continued $$R^1-\underset{\underset{R^3}{|}}{\overset{\overset{R^2}{|}}{Si}}-CH_2-X-\underset{\underset{R^4}{|}}{CH}-R^5$$

| Example No. | R¹ | R² | R³ | X | R⁴ | R⁵ | Physical Data |
|---|---|---|---|---|---|---|---|
| 257 | F₂CHO-pyridyl | H₃ | CH₃ | CH₂ | H | pyridyl-O-C₆H₄-F | |
| 258 | F₂CHO-pyridyl | CH₃ | CH₃ | CH₂ | H | (F)C₆H₃-O-C₆H₄-F | |
| 259 | F₂CHO-pyridyl | CH₃ | CH₃ | CH₂ | CN | (F)C₆H₃-O-C₆H₅ | |
| 260 | F₂CHO-pyridyl | CH₃ | CH₃ | O | H | C₆H₄-O-C₆H₅ | |
| 261 | F₂CHO-pyridyl | CH₃ | CH₃ | O | H | (F)C₆H₃-O-C₆H₅ | |
| 262 | F₂CHO-pyridyl | CH₃ | CH₃ | O | H | pyridyl-O-C₆H₅ | |
| 263 | F₂CHO-pyridyl | CH₃ | CH₃ | O | H | pyridyl-O-C₆H₄-F | |
| 264 | F₂CHO-pyridyl | CH₃ | CH₃ | O | CH₃ | C₆H₄-O-C₆H₅ | |
| 265 | F₂CHO-pyrimidyl | CH₃ | CH₃ | CH₂ | H | C₆H₄-O-C₆H₅ | |

-continued

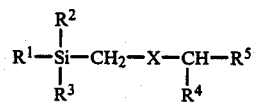

| Example No. | R¹ | R² | R³ | X | R⁴ | R⁵ | Physical Data |
|---|---|---|---|---|---|---|---|
| 266 | F₂CHO-(difluoromethoxy pyrimidinyl) | CH₃ | CH₃ | CH₂ | H | 2-fluorophenoxyphenyl | |
| 267 | F₂CHO-(difluoromethoxy pyrimidinyl) | CH₃ | CH₃ | CH₂ | H | (pyridinyloxy)phenyl | |
| 268 | F₂CHO-(difluoromethoxy pyrimidinyl) | CH₃ | CH₃ | CH₂ | H | (pyridinyloxy)-4-fluorophenyl | |
| 269 | F₂CHO-(difluoromethoxy pyrimidinyl) | CH₃ | CH₃ | CH₂ | H | 2-fluoro-(4-fluorophenoxy)phenyl | |
| 270 | F₂CHO-(difluoromethoxy pyrimidinyl) | CH₃ | CH₃ | CH₂ | CN | 2-fluorophenoxyphenyl | |
| 271 | F₂CHO-(difluoromethoxy pyrimidinyl) | CH₃ | CH₃ | O | H | phenoxyphenyl | |
| 272 | F₂CHO-(difluoromethoxy pyrimidinyl) | CH₃ | CH₃ | O | H | 2-fluorophenoxyphenyl | |
| 273 | F₂CHO-(difluoromethoxy pyrimidinyl) | CH₃ | CH₃ | O | H | (pyridinyloxy)phenyl | |
| 274 | F₂CHO-(difluoromethoxy pyrimidinyl) | CH₃ | CH₃ | O | H | (pyridinyloxy)-4-fluorophenyl | |

-continued $$R^1-\underset{\underset{R^3}{|}}{\overset{\overset{R^2}{|}}{Si}}-CH_2-X-\underset{\underset{R^4}{|}}{CH}-R^5$$

| Example No. | R¹ | R² | R³ | X | R⁴ | R⁵ | Physical Data |
|---|---|---|---|---|---|---|---|
| 275 | 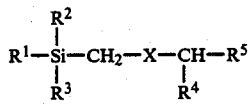 | CH₃ | CH₃ | O | CH₃ | 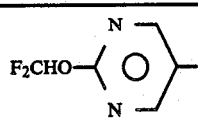 | |

C. Biological Examples

Example 1

Field beans (*Vicia faba*) which were heavily infested with Cowpea aphid (*Aphis craccivora*) were sprayed with aqueous dilutions of emulsion concentrates containing 1000 ppm of active compound until the stage where dripping commenced. After 3 days, the mortality was 100% in each case for the preparations containing the active compound of Examples 1, 2, 3, 5, 8, 9, 10, 13, 19, 20, 30, 46, 52, 100, 101, 106, 107, 156, 161 and 162.

Example 2

Bean plants (*Phaseolus vulgaris*) which were heavily infested with whitefly (*Trialeurodes vaporarierum*) were sprayed with aqueous dilutions of emulsion concentrates (1000 ppm of active compound) until dripping commenced. 14 days after the plants were placed in a greenhouse, they were inspected microscopically, with a result of 100% mortality in each case of the preparations containing the active compound of Examples 2, 8, 9, 13, 19, 46 and 101.

Example 3

Experimental procedure: analogous to Example 2
Experimental animals: *Tetranychus urticae* (two-spotted spider mite)
Experimental plants: *Phaseolus vulgaris* (Kidney bean)
Amount applied: 1000 ppm of active compound in the spray liquid
After 8 days, an activity of 100% mortality was observed for compound 9.

Example 4

Bean plants (*Phaseolus vulgaris*) which were heavily infested with citrus mealybug (*Pseudococcus citri*) were sprayed with aqueous dilutions of emulsion concentrates (1000 ppm of active compound in the spray liquid in each case) until the stage where dripping commenced. After standing for 7 days in a greenhouse at 20°-25° C., the inspection was carried out. 100% mortality was determined for the compounds according to Examples , 2, 3, 5, 8, 9, 100, 101, 106, 107 and 162.

Example 5

Milkweed bugs (*Oncopeltus fasciatus*) were treated with aqueous dilutions of emulsion concentrates (1000 ppm of active compound in the spray liquid in each case) of the active compounds of Examples 1, 2, 3, 5, 8, 9, 10, 13, 19, 20, 30, 46, 52, 100, 101, 106 and 162. The bugs were subsequently placed at room temperature in containers provided with lids which were permeable to air. 5 days after the treatment, the mortality was determined and was 100% in each individual case.

Example 6

The insides of the bases of Petri dishes coated with a synthetic nutrient medium were sprayed, after solidification of the feedstuff paste, in each case with 3 ml of an aqueous emulsion containing 2000 ppm of active compound. After the spray coating had dried and 10 larvae of the common cotton worm (*Prodenia litura*) were inserted, the dishes were stored for 7 days at 21° C. and the degree of action of the respective compound (expressed in % mortality) was determined. The compounds 2, 8, 9, 10, 18, 19, 30, 52, 100, 101, 106, and 107 produced an activity of 100% in each case in this test.

Example 7

Bean leaves (*Phaseolus vulgaris*) were treated with an aqueous emulsion of the compound of Example 9 in a concentration of 1000 ppm (based on the active compound) and placed with similarly treated larvae of the Mexican bean beetle (*Epilachna varivestis*) in observation cages. An evaluation after 48 hours showed 100% destruction of the experimental animals. The compounds according to Examples 1, 2, 8 and 19 proved similarly effective.

Example 8

1 ml of Example 9 as active compound in acetone with a concentration of 1000 ppm was applied evenly to the inside of the lid and the base of a Petri dish using a pipette, and the dish was left open until the solvent had evaporated completely. 10 houseflies (*Musca domestica*) were then placed in each of the Petri dishes, the dishes were closed using the lid, and a 100% destruction of the experimental animals was determined after 3 hours. The compounds according to Examples 1, 2, 100, 101, 106 and 107 also proved effective.

Example 9

1 ml of an active compound solution in acetone having a concentration of 2000 ppm was applied evenly to the inside of the lid and the base of a Petri dish using a pipette. After the solvent had evaporated completely, 10 larvae (L4) of the German cockroach (*Blatella germanica*) were inserted into each Petri dish, and the dishes were closed using the lids. After 72 hours, the action (expressed in % mortality) was determined. The compounds 1, 2, 3, 5, 8, 9, 10, 13, 19, 20, 30, 46, 52, 100, 101, 106 and 107 gave an activity of 100% in each case in this test.

We claim:

1. A compound of formula I, the optical isomers thereof, and the mixtures of these,

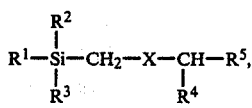

in which

X is $CH_2$ or O, $R^1$ is a pyridyl or pyrimidyl radical of formulae (A) or (B), wherein said pyridyl radical is bound to the Si atom in positions 2 or 3 and said pyridmidyl radical is bound to the Si atom in positions 2 or 5,

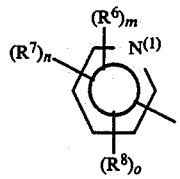

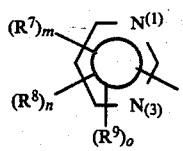

in which m, n and o are integers from 0 to 2 such that $0 \leq m+n+o \leq 3$, $R^6$, $R^7$, $R^8$ and $R^9$ may be the same or different and each is halogen, $(C_1-C_4)$alkyl, $(C_1-C_3)$alkoxy, $(C_1-C_3)$haloalkyl or $(C_1-C_3)$haloalkoxy, or two or the radicals $R^6$, $R^7$, $R^8$ and $R^9$, if in the ortho-position relative to one another, form a methylenedioxy, ethylenedioxy or $(C_3-C_5)$alkylene radical, $R^2$ and $R^3$ are $(C_1-C_3)$alkyl or $R^2$ and $R^3$ together are a $(C_3-C_5)$alkylene chain, $R^5$ is —H, —CN, —$CCl_3$, —C≡CH, $(C_1-C_4)$alkyl, F or

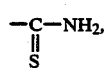

$R^5$ is a substituted penyl radical of formula (C)

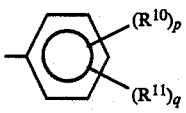

in which $R^{10}$ and $R^{11}$ may be the same or different and each is halogen, $(C_1-C_4)$alkyl, $(C_1-C_4)$alkoxy, $(C_1-C_4)$haloalkyl, phenyl N-pyrrolyl or a radical of formula (D)

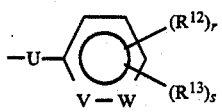

in which $R^{12}$ and $R^{13}$ may be the same or different and each is hydrogen, halogen, $(C_1-C_4)$alkyl, $(C_1-C_4)$alkoxy, $(C_1-C_4)$haloalkyl, U is —$CH_2$—, C=O, —O— or —S—, V and W are CH or N, where both V and W can simultaneously be CH but cannot simultaneously be N, and wherein in formulae (C) and (D) above, p and q are integers from 0 to 5 such that p+q is an integer from 1 to 5, r and s are 0, 1 or 2 such that r+s is 0, 1 or 2, and if $R^{10}$ or $R^{11}$ are a radical of formula (D), then p and q are 0 or 1 such that p+q is 1 or 2, or $R^5$ is a pyridyl radical of formula (E)

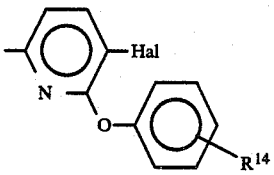

in which $R^{14}$ is F, Cl, Br, $(C_1-C_4)$alkyl, $(C_1-C_4)$alkoxy, $(C_1-C_4)$haloalkyl, and Hal is halogen or hydrogen.

2. The compound of formula I as claimed in claim 1 wherein in the radical of formula (D), U is O and in the pyridyl radical of formula (E), Hal is fluorine.

3. A compound of formula I as claimed in claim 1 in which $R^1$ is a monosubstituted or dibustituted pyridyl or pyridmidyl radical wherein the pyridyl radical is bound to the Si atom in positions 2 or 3 and the pyrimidyl radical is bound to the Si atom in positions 2 or 5, the substituents $R^6$, $R^7$, $R^8$ or $R^9$ are oriented in the para or meta position to the Si linking point, $R^2$ and $R^3$ are $CH_3$, $R^4$ is hydrogen and $R^5$ is a radical of formula

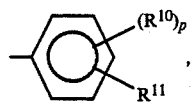

wherein $(R^{10})_p$ is hydrogen or 4-fluorine and $R^{11}$ is the radical

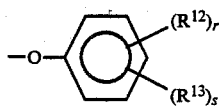

wherein $R^{12}$ and $R^{13}$ are halogen or hydrogen and r+s is 0, 1 or 2.

4. A compound of formula I as claimed in claim 1, in which $R^5$ is a pyridyl radical of formula E

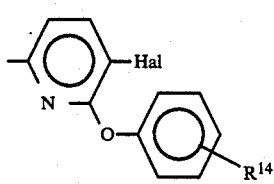

in which $R^{14}$ is F, Cl, Br, $(C_1-C_4)$-alkyl, $(C_1-C_4)$alkoxy or $(C_1-C_4)$haloalkyl, and Hal is halogen or hydrogen.

5. A compound as claimed in claim 3 wherein $R^{12}$ and $R^{13}$ are fluorine.

6. A compound as claimed in claim 4 wherein Hal is fluorine.

7. An insecticidal, acaricidal or nematocidal agent which comprises an effective amount of a compound as claimed in claim 1 and an inert carrier.

8. A method for combatting insect pests, acarids or nematodes which comprises applying an effective amount of a compound as claimed in claim 1 to said insect pests, acarids or nematodes and the surfaces, plants or substrates infected by them.

* * * * *